United States Patent
Zhang et al.

(10) Patent No.: US 10,905,704 B2
(45) Date of Patent: Feb. 2, 2021

(54) AGENTS AND METHODS USING THEREOF FOR THE PREVENTION AND TREATMENT OF STEM CELL MUSCLE DISORDERS

(71) Applicant: ECOLE POLYTECHNIQUE FEDERALE DE LAUSANNE (EPFL), Lausanne (CH)

(72) Inventors: Hongbo Zhang, Guangzhou (CN); Keir Menzies, Luskville (CA); Johan Auwerx, Buchillon (CH); Dongryeol Ryu, Busan (KR)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 15/758,365

(22) PCT Filed: Sep. 7, 2016

(86) PCT No.: PCT/EP2016/071044
§ 371 (c)(1),
(2) Date: Mar. 8, 2018

(87) PCT Pub. No.: WO2017/042198
PCT Pub. Date: Mar. 16, 2017

(65) Prior Publication Data
US 2018/0360862 A1    Dec. 20, 2018

(30) Foreign Application Priority Data
Sep. 8, 2015   (EP) .................................... 15184341

(51) Int. Cl.
*A61K 31/706*   (2006.01)
*A61K 35/34*    (2015.01)
(Continued)

(52) U.S. Cl.
CPC ............ *A61K 31/706* (2013.01); *A23L 33/10* (2016.08); *A23L 33/13* (2016.08); *A61K 31/165* (2013.01);
(Continued)

(58) Field of Classification Search
CPC .. A61K 38/1825; A61K 31/165; A61K 31/65; A61K 31/706; A61K 35/34;
(Continued)

(56) References Cited

U.S. PATENT DOCUMENTS

| 5,045,538 A | 9/1991 | Schneider et al. |
| 9,180,134 B2 | 11/2015 | Auwerx et al. |

(Continued)

FOREIGN PATENT DOCUMENTS

| WO | WO 2007/008548 | 1/2007 |
| WO | WO 2013/024467 | 2/2013 |

(Continued)

OTHER PUBLICATIONS

Tyynismaa et al. Mutant mitochondrial helicase Twinkle causes multiple mtDNA deletions and a late-onset mitochondrial disease in mice. PNAS (2005), 102(49), 17687-17692. (Year: 2005).*

(Continued)

*Primary Examiner* — Sean C. Barron
(74) *Attorney, Agent, or Firm* — Saliwanchik, Lloyd & Eisenschenk

(57) ABSTRACT

The present invention relates to agents that induce mitochondrial unfolded protein response (UPR mt) in muscle stem cells and prevents or reverse process of muscle stem cell senescence. Further, the invention relates to methods and compositions useful in the prevention and/or treatment of muscle stem senescence.

6 Claims, 11 Drawing Sheets

Specification includes a Sequence Listing.

(51) Int. Cl.
    A23L 33/10    (2016.01)
    A61K 31/165   (2006.01)
    A61K 45/06    (2006.01)
    A61K 31/65    (2006.01)
    A61K 38/18    (2006.01)
    A23L 33/13    (2016.01)
    A61P 21/00    (2006.01)
    C12N 5/077    (2010.01)

(52) U.S. Cl.
    CPC .............. A61K 31/65 (2013.01); A61K 35/34 (2013.01); A61K 38/1825 (2013.01); A61K 45/06 (2013.01); A61P 21/00 (2018.01); C12N 5/0658 (2013.01); C12N 2501/10 (2013.01); C12N 2501/999 (2013.01)

(58) Field of Classification Search
    CPC ..... A61K 45/06; A61K 2300/00; A23L 33/10; A23L 33/13; C12N 5/0658; C12N 2501/999; C12N 2501/10; A61P 21/00; A61P 31/165; A23V 2002/00
    See application file for complete search history.

(56) References Cited

U.S. PATENT DOCUMENTS

| | | | |
|---|---|---|---|
| 2011/0224128 A1* | 9/2011 | Whalen | A61K 31/445 514/1.1 |
| 2017/0252362 A1 | 9/2017 | Vannini et al. | |
| 2019/0054098 A1 | 2/2019 | Zhang et al. | |

FOREIGN PATENT DOCUMENTS

| | | |
|---|---|---|
| WO | WO 2014/168973 | 10/2014 |
| WO | WO 2015/186068 | 12/2015 |
| WO | WO 2016/038011 | 3/2016 |
| WO | WO 2016/149672 | 9/2016 |
| WO | WO 2017/042196 | 3/2017 |

OTHER PUBLICATIONS

Lee et al. Nicotinamide Riboside Ameliorates Hepatic Metaflammation by Modulating NLRP3 Inflammasome in a Rodent Model of Type 2 Diabetes. Journal of Medicinal Food (epub May 2015), 18(11), 12071213. (Year: 2015).*
Mursic et al. In Vitro and In Vivo Susceptibility of Borrelia burgdorferi. Eur. J. Microbiol. (1987), 6(4), 424-426. (Year: 1987).*
Myopathy (in R. M. Youngson, Collins Dictionary of Medicine (4th ed.). Collins (2005). (Year: 2005).*
Fukui et al. In Vitro and in Vivo Antibacterial Activities of Florfenicol, a New Fluorinated Analog of Thiamphenicol, Against Fish Pathogens. Fish Pathology (1987), 22(4), 201-207. (Year: 1987).*
Bernet, J. D. et al. "P38 MAPK signaling underlies a cell autonomous loss of stem cell self-renewal in aged skeletal muscle" Nature Medicine, Mar. 2014, pp. 1-24, vol. 20, No. 3.
Boitano, A. E. et al. "Aryl Hydrocarbon Receptor Antagonists Promote the Expansion of Human Hematopoietic Stem Cells" Science, Sep. 10, 2010, pp. 1-10, vol. 329, No. 5997.
Burd, C. E. et al. "Monitoring Tumorigenesis and Senescence In Vivo with a p16$^{INK4a}$-Luciferase Model" Cell, Jan. 17, 2013, pp. 340-351, vol. 152.
Cantó, C. et al. "The NAD$^+$ Precursor Nicotinamide Riboside Enhances Oxidative Metabolism and Protects against High-Fat Diet-Induced Obesity" Cell Metabolism, Jun. 6, 2012, pp. 838-847, vol. 15.
Cerletti, M. et al. "Short-term calorie restriction enhances skeletal muscle stem cell function" Cell Stem Cell, May 4, 2012, pp. 1-10, vol. 10, No. 5.
Chakkalakal, J. V. et al. "The aged niche disrupts muscle stem cell quiescence" Nature, Oct. 18, 2012, pp. 1-19, vol. 490, No. 7420.

Coates, P. J. et al. "Mammalian Prohibitin Proteins Respond to Mitochondrial Stress and Decrease during Cellular Senescence" Experimental Cell Research, 2001, pp. 262-273, vol. 265.
Conboy, I. M. et al. "Rejuvenation of aged progenitor cells by exposure to a young systemic environment" Nature, Feb. 17, 2005, pp. 760-764, vol. 433.
Cosgrove, B. D. et al. "Rejuvenation of the aged muscle stem cell population restores strength to injured aged muscles" Nature Medicine, Mar. 2014, pp. 1-31, vol. 20, No. 3.
Folmes, C. D. L. et al. "Metabolic Plasticity in Stem Cell Homeostasis and Differentiation" Cell Stem Cell, Nov. 2, 2012, pp. 1-19, vol. 11, No. 5.
Frederick, D. W. et al. "Loss of NAD Homeostasis Leads to Progressive and Reversible Degeneration of Skeletal Muscle" Cell Metabolism, Aug. 9, 2016, pp. 269-282, vol. 24.
Fulco, M. et al. "Sir2 Regulates Skeletal Muscle Differentiation as a Potential Sensor of the Redox State" Molecular Cell, Jul. 2003, pp. 51-62, vol. 12.
Gomes, A. P. et al. "Declining NAD$^+$ Induces a Pseudohypoxic State Disrupting Nuclear-Mitochondrial Communication during Aging" Cell, Dec. 19, 2013, pp. 1-28, vol. 155, No. 7.
Hara, E. et al. "Regulation of p16$^{CDKN2}$ Expression and Its Implications for Cell Immortalization and Senescence" Molecular and Cellular Biology, Mar. 1996, pp. 859-867, vol. 16, No. 3.
Jang, Y. C. et al. "Skeletal Muscle Stem Cells: Effects of Aging and Metabolism on Muscle Regenerative Function" Cold Spring Harbor Symposia on Quantitative Biology, Sep. 29, 2011, pp. 101-111, vol. 76.
Khan, N. A. et al. "Effective treatment of mitochondrial myopathy by nicotinamide riboside, a vitamin B3" EMBO Molecular Medicine, Apr. 6, 2014, pp. 721-731, vol. 6, No. 6.
Kuilman, T. et al. "The essence of senescence" Genes & Development, 2010, pp. 2463-2479, vol. 24.
Lightowlers, R. N. et al. "Salvaging hope: Is increasing NAD$^+$ a key to treating mitochondrial myopathy?" EMBO Molecular Medicine, May 16, 2014, pp. 705-707, vol. 6, No. 6.
Liu, L. et al. "Chromatin Modifications as Determinants of Muscle Stem Cell Quiescence and Chronological Aging" Cell Reports, Jul. 11, 2013, pp. 1-30, vol. 4, No. 1.
López-Otín, C. et al. "The Hallmarks of Aging" Cell, Jun. 6, 2013, pp. 1-47, vol. 153, No. 6.
Mercer, T. R. et al. "The human mitochondrial transcriptome" Cell, Aug. 19, 2011, pp. 1-20, vol. 146, No. 4.
Mouchiroud, L. et al. "The NAD$^+$/sirtuin pathway modulates longevity through activation of mitochondrial UPR and FOXO signaling" Cell, Jul. 18, 2013, pp. 1-20, vol. 154, No. 2.
Musarò, A. et al. "The Role of Igf-1 on Muscle Wasting: a Therapeutic Approach" Basic and Applied Myology, 2004, pp. 29-32, vol. 14, No. 1.
Pagliarini, D. J. et al. "A mitochondrial protein compendium elucidates complex I disease biology" Cell, Jul. 11, 2008, pp. 1-20, vol. 134, No. 1.
Piegari, E. et al. "Doxorubicin induces senescence and impairs function of human cardiac progenitor cells" Basic Research in Cardiology, 2013, pp. 1-18, vol. 108, No. 334.
Pirinen, E. et al. "Pharmacological Inhibition of Poly(ADP-Ribose) Polymerases Improves Fitness and Mitochondrial Function in Skeletal Muscle" Cell Metabolism, Jun. 3, 2014, pp. 1-15, vol. 19, No. 6.
Price, F. D. et al. "Inhibition of JAK/STAT signaling stimulates adult satellite cell function" Nature Medicine, Oct. 2014, pp. 1-26, vol. 20, No. 10.
Quinn, K. P. et al. "Quantitative metabolic imaging using endogenous fluorescence to detect stem cell differentiation" Scientific Reports, Dec. 5, 2013, pp. 1-10, vol. 3, No. 3432.
Ryall, J. G. et al. "The NAD$^+$-Dependent SIRT1 Deacetylase Translates a Metabolic Switch into Regulatory Epigenetics in Skeletal Muscle Stem Cells" Cell Stem Cell, Feb. 5, 2015, pp. 1-23, vol. 16, No. 2.
Ryu, D. et al. "NAD$^+$ repletion improves muscle function in muscular dystrophy and counters global PARylation" Science Translational Medicine, Oct. 19, 2016, pp. 1-29, vol. 8, No. 361.

(56) References Cited

OTHER PUBLICATIONS

Sartore, S. et al. "Fetal myosin heavy chains in regenerating muscle" *Nature*, Jul. 15, 1982, pp. 294-296, vol. 298.

Shefer, G. et al. "Exercise Running and Tetracycline as Means to Enhance Skeletal Muscle Stem Cell Performance After External Fixation" *Journal of Cellular Physiology*, 2007, pp. 265-275, vol. 215, No. 1.

Sickmann, A. et al. "The proteome of *Saccharomyces cerevisiae* mitochondria" *PNAS*, Nov. 11, 2003, pp. 13207-13212, vol. 100, No. 23.

Sousa-Victor, P. et al. "Geriatric muscle stem cells switch reversible quiescence into senescence" *Nature*, Feb. 20, 2014, pp. 316-321 and Extended Data pp. 1-9, vol. 506.

Stein, L. R. et al. "Specific ablation of Nampt in adult neural stem cells recapitulates their functional defects during aging" *The EMBO Journal*, May 8, 2014, pp. 1321-1340, vol. 33, No. 12.

Tabebordbar, M. et al. "Skeletal Muscle Degenerative Diseases and Strategies for Therapeutic Muscle Repair" *Annual Review of Pathology: Mechanisms of Disease*, 2013, pp. 441-475, vol. 8.

Tierney, M. T. et al. "STAT3 signaling controls satellite cell expansion and skeletal muscle repair" *Nature Medicine*, Oct. 2014, pp. 1-18, vol. 20, No. 10.

Tsuchida, K. "Myostatin inhibition by a follistatin-derived peptide ameliorates the pathophysiology of muscular dystrophy model mice" *Acta Myologica*, 2008, pp. 14-18, vol. XXVII.

Wagers, A. J. et al. "Plasticity of Adult Stem Cells" *Cell*, Mar. 5, 2004, pp. 639-648, vol. 116.

Yin, H. et al. "Satellite Cells and the Muscle Stem Cell Niche" *Physiological Reviews*, Jan. 2013, pp. 1-71, vol. 93, No. 1.

Yoshino, J. et al. "Nicotinamide mononucleotide, a key $NAD^+$ intermediate, treats the pathophysiology of diet- and age-induced diabetes in mice" *Cell Metabolism*, Oct. 5, 2011, pp. 1-15, vol. 14, No. 4.

Zhang, H. et al. "$NAD^+$ repletion improves mitochondrial and stem cell function and enhances life span in mice" *Science*, Jun. 17, 2016, pp. 1436-1443, vol. 352, No. 6292.

Written Opinion in International Application No. PCT/EP2016/071044, dated Mar. 13, 2017, pp. 1-11.

\* cited by examiner

SEQUENCE LISTING

<160> NUMBER OF SEQ ID NOS: 46

<210> SEQ ID NO 1
<211> LENGTH: 21
<212> TYPE: DNA
<213> ORGANISM: Artificial Sequence
<220> FEATURE:
<223> OTHER INFORMATION: 36b4 forward primer

<400> SEQUENCE: 1
agattcggga tatgctgttg g                                              21

<210> SEQ ID NO 2
<211> LENGTH: 21
<212> TYPE: DNA
<213> ORGANISM: Artificial Sequence
<220> FEATURE:
<223> OTHER INFORMATION: 36b4 reverse primer

<400> SEQUENCE: 2
aaagcctgga agaaggaggt c                                              21

<210> SEQ ID NO 3
<211> LENGTH: 20
<212> TYPE: DNA
<213> ORGANISM: Artificial Sequence
<220> FEATURE:
<223> OTHER INFORMATION: Ndufb5 forward primer

<400> SEQUENCE: 3
cttcgaactt cctgctcctt                                                20

<210> SEQ ID NO 4
<211> LENGTH: 19
<212> TYPE: DNA
<213> ORGANISM: Artificial Sequence
<220> FEATURE:
<223> OTHER INFORMATION: Ndufb5 reverse primer

```
<400> SEQUENCE: 4
ggccctgaaa agaactacg                                               19

<210> SEQ ID NO 5
<211> LENGTH: 22
<212> TYPE: DNA
<213> ORGANISM: Artificial Sequence
<220> FEATURE:
<223> OTHER INFORMATION: Sdha forward primer

<400> SEQUENCE: 5
ggaacactcc aaaaacagac ct                                           22

<210> SEQ ID NO 6
<211> LENGTH: 23
<212> TYPE: DNA
<213> ORGANISM: Artificial Sequence
<220> FEATURE:
<223> OTHER INFORMATION: Sdha reverse primer

<400> SEQUENCE: 6
ccaccactgg gtattgagta gaa                                          23

<210> SEQ ID NO 7
<211> LENGTH: 20
<212> TYPE: DNA
<213> ORGANISM: Artificial Sequence
<220> FEATURE:
<223> OTHER INFORMATION: Sdhc forward primer

<400> SEQUENCE: 7
gctgcgttct tgctgagaca                                              20

<210> SEQ ID NO 8
<211> LENGTH: 21
<212> TYPE: DNA
<213> ORGANISM: Artificial Sequence
<220> FEATURE:
<223> OTHER INFORMATION: Sdhc reverse primer

<400> SEQUENCE: 8
atctcctcct tagctgtggt t                                            21

<210> SEQ ID NO 9
<211> LENGTH: 20
<212> TYPE: DNA
<213> ORGANISM: Artificial Sequence
<220> FEATURE:
<223> OTHER INFORMATION: Cox5b forward primer

<400> SEQUENCE: 9
aagtgcatct gcttgtctcg                                              20

<210> SEQ ID NO 10
<211> LENGTH: 20
<212> TYPE: DNA
<213> ORGANISM: Artificial Sequence
<220> FEATURE:
<223> OTHER INFORMATION: Cox5b reverse primer

<400> SEQUENCE: 10
gtcttccttg gtgcctgaag                                              20

<210> SEQ ID NO 11
<211> LENGTH: 21
```

<212> TYPE: DNA
<213> ORGANISM: Artificial Sequence
<220> FEATURE:
<223> OTHER INFORMATION: Atp5b forward primer

<400> SEQUENCE: 11
ggttcatcct gccagagact a                                             21

<210> SEQ ID NO 12
<211> LENGTH: 21
<212> TYPE: DNA
<213> ORGANISM: Artificial Sequence
<220> FEATURE:
<223> OTHER INFORMATION: Atp5b reverse primer

<400> SEQUENCE: 12
aatccctcat cgaactggac g                                             21

<210> SEQ ID NO 13
<211> LENGTH: 20
<212> TYPE: DNA
<213> ORGANISM: Artificial Sequence
<220> FEATURE:
<223> OTHER INFORMATION: Mdh2 forward primer

<400> SEQUENCE: 13
ttgggcaacc cctttcactc                                               20

<210> SEQ ID NO 14
<211> LENGTH: 22
<212> TYPE: DNA
<213> ORGANISM: Artificial Sequence
<220> FEATURE:
<223> OTHER INFORMATION: Mdh2 reverse primer

<400> SEQUENCE: 14
gcctttcaca tttgctctgg tc                                            22

<210> SEQ ID NO 15
<211> LENGTH: 21
<212> TYPE: DNA
<213> ORGANISM: Artificial Sequence
<220> FEATURE:
<223> OTHER INFORMATION: Idh2 forward primer

<400> SEQUENCE: 15
ggagaagccg gtagtggaga t                                             21

<210> SEQ ID NO 16
<211> LENGTH: 20
<212> TYPE: DNA
<213> ORGANISM: Artificial Sequence
<220> FEATURE:
<223> OTHER INFORMATION: Idh2 reverse primer

<400> SEQUENCE: 16
ggtctggtca cggtttggaa                                               20

<210> SEQ ID NO 17
<211> LENGTH: 20
<212> TYPE: DNA
<213> ORGANISM: Artificial Sequence
<220> FEATURE:
<223> OTHER INFORMATION: Idh3a forward primer

<400> SEQUENCE: 17

```
cccatcccag tttgatgttc                                              20
```

<210> SEQ ID NO 18
<211> LENGTH: 20
<212> TYPE: DNA
<213> ORGANISM: Artificial Sequence
<220> FEATURE:
<223> OTHER INFORMATION: Idh3a reverse primer

<400> SEQUENCE: 18

```
accgattcaa agatggcaac                                              20
```

<210> SEQ ID NO 19
<211> LENGTH: 19
<212> TYPE: DNA
<213> ORGANISM: Artificial Sequence
<220> FEATURE:
<223> OTHER INFORMATION: Cdkn1a forward primer

<400> SEQUENCE: 19

```
gtgggtctga ctccagccc                                               19
```

<210> SEQ ID NO 20
<211> LENGTH: 20
<212> TYPE: DNA
<213> ORGANISM: Artificial Sequence
<220> FEATURE:
<223> OTHER INFORMATION: Cdkn1a reverse primer

<400> SEQUENCE: 20

```
ccttctcgtg agacgcttac                                              20
```

<210> SEQ ID NO 21
<211> LENGTH: 20
<212> TYPE: DNA
<213> ORGANISM: Artificial Sequence
<220> FEATURE:
<223> OTHER INFORMATION: Mki67 forward primer

<400> SEQUENCE: 21

```
ttggaaagga accatcaagg                                              20
```

<210> SEQ ID NO 22
<211> LENGTH: 20
<212> TYPE: DNA
<213> ORGANISM: Artificial Sequence
<220> FEATURE:
<223> OTHER INFORMATION: Mki67 reverse primer

<400> SEQUENCE: 22

```
tttctgccag tgtgctgttc                                              20
```

<210> SEQ ID NO 23
<211> LENGTH: 20
<212> TYPE: DNA
<213> ORGANISM: Artificial Sequence
<220> FEATURE:
<223> OTHER INFORMATION: Cdk4 forward primer

<400> SEQUENCE: 23

```
ccggttgaga ccattaagga                                              20
```

<210> SEQ ID NO 24
<211> LENGTH: 20
<212> TYPE: DNA
<213> ORGANISM: Artificial Sequence

```
<220> FEATURE:
<223> OTHER INFORMATION: Cdk4 reverse primer

<400> SEQUENCE: 24
cacgggtgtt gcgtatgtag                                                  20

<210> SEQ ID NO 25
<211> LENGTH: 21
<212> TYPE: DNA
<213> ORGANISM: Artificial Sequence
<220> FEATURE:
<223> OTHER INFORMATION: Ccna2 forward primer

<400> SEQUENCE: 25
aagagaatgt caaccccgaa a                                                21

<210> SEQ ID NO 26
<211> LENGTH: 20
<212> TYPE: DNA
<213> ORGANISM: Artificial Sequence
<220> FEATURE:
<223> OTHER INFORMATION: Ccna2 reverse primer

<400> SEQUENCE: 26
acccgtcgag tcttgagctt                                                  20

<210> SEQ ID NO 27
<211> LENGTH: 22
<212> TYPE: DNA
<213> ORGANISM: Artificial Sequence
<220> FEATURE:
<223> OTHER INFORMATION: Ccnd1 forward primer

<400> SEQUENCE: 27
gagcgtggtg gctgcgatgc aa                                               22

<210> SEQ ID NO 28
<211> LENGTH: 25
<212> TYPE: DNA
<213> ORGANISM: Artificial Sequence
<220> FEATURE:
<223> OTHER INFORMATION: Ccnd1 reverse primer

<400> SEQUENCE: 28
ggcttgactc cagaagggct tcaat                                            25

<210> SEQ ID NO 29
<211> LENGTH: 20
<212> TYPE: DNA
<213> ORGANISM: Artificial Sequence
<220> FEATURE:
<223> OTHER INFORMATION: Ccne1 forward primer

<400> SEQUENCE: 29
caaagcccaa gcaaagaaag                                                  20

<210> SEQ ID NO 30
<211> LENGTH: 20
<212> TYPE: DNA
<213> ORGANISM: Artificial Sequence
<220> FEATURE:
<223> OTHER INFORMATION: Ccne1 reverse primer

<400> SEQUENCE: 30
ccactgtctt tggaggcaat                                                  20
```

```
<210> SEQ ID NO 31
<211> LENGTH: 20
<212> TYPE: DNA
<213> ORGANISM: Artificial Sequence
<220> FEATURE:
<223> OTHER INFORMATION: Cdc6 forward primer

<400> SEQUENCE: 31
gacacaagct accatggttt                                                 20

<210> SEQ ID NO 32
<211> LENGTH: 21
<212> TYPE: DNA
<213> ORGANISM: Artificial Sequence
<220> FEATURE:
<223> OTHER INFORMATION: Cdc6 reverse primer

<400> SEQUENCE: 32
caggctggac gtttctaagt t                                               21

<210> SEQ ID NO 33
<211> LENGTH: 21
<212> TYPE: DNA
<213> ORGANISM: Artificial Sequence
<220> FEATURE:
<223> OTHER INFORMATION: IL6 forward primer

<400> SEQUENCE: 33
ggtgacaacc acggccttcc c                                               21

<210> SEQ ID NO 34
<211> LENGTH: 23
<212> TYPE: DNA
<213> ORGANISM: Artificial Sequence
<220> FEATURE:
<223> OTHER INFORMATION: IL6 reverse primer

<400> SEQUENCE: 34
aagcctccga cttgtgaagt ggt                                             23

<210> SEQ ID NO 35
<211> LENGTH: 20
<212> TYPE: DNA
<213> ORGANISM: Artificial Sequence
<220> FEATURE:
<223> OTHER INFORMATION: IL18 forward primer

<400> SEQUENCE: 35
gtgaacccca gaccagactg                                                 20

<210> SEQ ID NO 36
<211> LENGTH: 22
<212> TYPE: DNA
<213> ORGANISM: Artificial Sequence
<220> FEATURE:
<223> OTHER INFORMATION: IL18 reverse primer

<400> SEQUENCE: 36
cctggaacac gtttctgaaa ga                                              22

<210> SEQ ID NO 37
<211> LENGTH: 22
<212> TYPE: DNA
<213> ORGANISM: Artificial Sequence
<220> FEATURE:
<223> OTHER INFORMATION: Hsp60 forward primer
```

```
<400> SEQUENCE: 37
acagtccttc gccagatgag ac                                              22

<210> SEQ ID NO 38
<211> LENGTH: 20
<212> TYPE: DNA
<213> ORGANISM: Artificial Sequence
<220> FEATURE:
<223> OTHER INFORMATION: Hsp60 reverse primer

<400> SEQUENCE: 38
tggattagcc cctttgctga                                                 20

<210> SEQ ID NO 39
<211> LENGTH: 22
<212> TYPE: DNA
<213> ORGANISM: Artificial Sequence
<220> FEATURE:
<223> OTHER INFORMATION: Hsp10 forward primer

<400> SEQUENCE: 39
ctgacaggtt caatctctcc ac                                              22

<210> SEQ ID NO 40
<211> LENGTH: 20
<212> TYPE: DNA
<213> ORGANISM: Artificial Sequence
<220> FEATURE:
<223> OTHER INFORMATION: Hsp10 reverse primer

<400> SEQUENCE: 40
aggtggcatt atgcttccag                                                 20

<210> SEQ ID NO 41
<211> LENGTH: 20
<212> TYPE: DNA
<213> ORGANISM: Artificial Sequence
<220> FEATURE:
<223> OTHER INFORMATION: Clpp forward primer

<400> SEQUENCE: 41
cacaccaagc agagcctaca                                                 20

<210> SEQ ID NO 42
<211> LENGTH: 20
<212> TYPE: DNA
<213> ORGANISM: Artificial Sequence
<220> FEATURE:
<223> OTHER INFORMATION: Clpp reverse primer

<400> SEQUENCE: 42
tccaagatgc caaactcttg                                                 20

<210> SEQ ID NO 43
<211> LENGTH: 20
<212> TYPE: DNA
<213> ORGANISM: Artificial Sequence
<220> FEATURE:
<223> OTHER INFORMATION: Phb forward primer

<400> SEQUENCE: 43
tcgggaagga gttcacagag                                                 20

<210> SEQ ID NO 44
```

```
<211> LENGTH: 20
<212> TYPE: DNA
<213> ORGANISM: Artificial Sequence
<220> FEATURE:
<223> OTHER INFORMATION: Phb reverse primer

<400> SEQUENCE: 44
cagccttttc caccacaaat                                               20

<210> SEQ ID NO 45
<211> LENGTH: 20
<212> TYPE: DNA
<213> ORGANISM: Artificial Sequence
<220> FEATURE:
<223> OTHER INFORMATION: Phb2 forward primer

<400> SEQUENCE: 45
caaggacttc agcctcatcc                                               20

<210> SEQ ID NO 46
<211> LENGTH: 20
<212> TYPE: DNA
<213> ORGANISM: Artificial Sequence
<220> FEATURE:
<223> OTHER INFORMATION: Phb2 reverse primer

<400> SEQUENCE: 46
gccacttgct tggcttctac                                               20
```

AGENTS AND METHODS USING THEREOF FOR THE PREVENTION AND TREATMENT OF STEM CELL MUSCLE DISORDERS

CROSS-REFERENCE TO RELATED APPLICATION

This application is the U.S. national stage application of International Patent Application No. PCT/EP2016/071044, filed Sep. 7, 2016.

The Sequence Listing for this application is labeled "Seq-List.txt" which was created on Feb. 9, 2018 and is 9 KB. The entire content of the sequence listing is incorporated herein by reference in its entirety.

FIELD OF THE INVENTION

The present invention relates generally to the field of muscle stem cell medicine and in particular regenerative therapies and muscle transplantation. In particular, the invention relates to methods and compositions useful in the regeneration of damage human tissue, ex vivo propagation of stem/progenitor cells and in the treatment of muscle diseases.

BACKGROUND OF THE INVENTION

In adults, tissue homeostasis is highly dependent on adult stem cells (SCs) function in multiple tissues. These adult SCs are not only essential in continuously-proliferating tissues, such as hematopoietic-, intestinal- and skin-systems, but also in normally quiescent tissues, such as skeletal muscle and brain that require regeneration following damage or with disease (Wagers and Weissman, 2004, *Cell*, 116: 639). Adult stem cells (SCs) are essential for tissue maintenance and regeneration yet are susceptible to SC senescence during aging that is a decline in adult SC quantity and function. SC senescence is at least partly responsible for the loss of tissue homeostasis and regenerative capacity (Kuilman et al., 2010, *Genes & Development*, 24: 2463; Lopez-Otin et al., 2013, *Cell* 153: 1194).

With respect to skeletal muscle, homeostasis and regeneration depends on the normally quiescent muscle stem cells (MuSCs), which are activated upon muscle damage to expand and give rise to differentiated progeny that regenerate damaged muscle fibers (Yin et al., 2013, *Physiological Reviews*, 93: 23; Tabebordbar et al., 2013, *Annual Review of Pathology*, 8: 441). These responses are blunted in aged muscle due to a quantitative and qualitative decline in MuSCs (Tang et al., 2011, *Cold spring Harbor symposia on quantitative biology* 76: 1001; Price et al., 2014, *Nature Med.*, 20: 1094). In aging, MuSC dysfunction may be attributed to both extrinsic signals (Conboy et al., 2005, *Nature* 433: 760; Chakkalakal et al., 2012, *Nature*, 490: 335) and/or intrinsic cellular senescence signalling pathways (Sousa-Victor et al., 2014, *Nature*, 506: 316). One general regulator of cellular senescence, cyclin-dependent kinase inhibitor 2A (CDKN2A, p16$^{INK4A}$), is increasingly expressed in geriatric MuSCs (Burd et al., 2013, *Cell*, 152: 316), eliciting permanent cell cycle withdrawal and senescence of MuSCs in very old mice (Sousa-Victor et al., supra). However, before this stage, reductions in MuSC number and function can already be observed (Tang et al., supra; Sousa-Victor et al., supra) indicating that MuSC senescence may be initiated at an earlier time point. Several recent reports support the idea that pre-geriatric mice, approximately two-years-old, can exhibit features of MuSC senescence (Price et al., supra; Bernet et al., 2014, *Nature Med.*, 20: 265; Cosgrove et al., 2014, *Nature Med.*, 20: 255; Tierney et al., 2014, *Nature Med.*, 20: 1182; Liu et al., 2013, *Cell Rep.*, 4: 189). However, the early mechanisms that instigate MuSC senescence are still largely unknown.

One of the hallmarks of organismal aging is the appearance of mitochondrial dysfunction (Kuilman et al., supra; Lopez-Otin et al., supra). Recent evidence has shown that mitochondrial dysfunction, induced by calorie-dense diets or aging, can result from oxidized nicotinamide adenine dinucleotide (NAD$^+$) depletion, while NAD$^+$ repletion, using precursors such as nicotinamide riboside (NR), can reverse this process (Canto et al., 2012, *Cell Metabolism*, 15: 1034; Pirinen et al., 2014, *Cell Metabolism*, 19: 1034; Mouchiroud et al., 2013, *Cell*, 154: 430; Yoshino et al., 2011, *Cell Metabolism* 14: 528; Gomes et al., 2013, *Cell*, 155:1624). It is generally assumed that stem cells rely predominantly on glycolysis for energy, a process that would reduce cellular NAD$^+$ (Folmes et al., 2012, *Cell Stem Cell*, 11: 596). However, mitochondrial function was linked to muscle and neural stem cell maintenance and activation (Cerletti et al., 2012, *Cell Stem Cell*, 10: 525; Ryall et al., 2015, *STEM* 16: 171, Stein et al., 2014, *EMBO J.*, 33: 1321), yet its role in SC senescence is unknown.

Disorders that are related to muscle stem cell senescence include muscle dystrophy diseases, such as Duchenne's muscular dystrophy (DMD), Becker's muscular dystrophy (BMD), Congenital muscular dystrophy, Distal muscular dystrophy, Emery-Dreifuss' muscular dystrophy, Facio-scapulo-humeral muscular dystrophy, Limb-girdle muscular dystrophy, Myotonic muscular dystrophy and Oculopharyngeal muscular dystrophy. It further includes other inherited myopathies, such as myotonia, congenital myopathies (includes nemaline myopathy, multi/minicore myopathy, centronuclear myopathy), metabolic myopathies (includes glycogen storage diseases and lipid storage disorder), inflammatory myopathies, such as dermatomyositis, polymyositis, inclusion body myositis and auto-immune myositis. These diseases further include muscle frailty and sarcopenia in aging (Sousa-Victor et al., supra) and other acquired myopathies, such as drug/toxic agents-induced myopathy, alcoholic myopathy, myositis ossificans, rhabdomyolysis and myoglobinurias. Other diseases linked to muscle stem cell senescence include muscle wasting induced by nutritional deficiencies. Diseases linked to muscle stem cell senescence may be developed in the context of other diseases, such as chronic obstructive pulmonary disease (COPD), chronic inflammatory syndromes, and cachexia of cancer. Further, diseases linked to muscle stem cell senescence may be developed as a result of clinical treatments that use compounds such as anthracyclines (i.e. doxorubicin) that can cause severe skeletal muscle and cardiac muscle toxicity leading to heart failure (Piegari et al., 2013, *Basic Res Cardiol.* 108(2): 334).

In order to prevent some muscle stem senescence and related muscular dystrophies, some dietary interventions such as creatine supplements, resveratrol, protein-rich diets, and exercise regimens are recommended and the use mesenchymal stem cells transplantation or MuSC transplantation are being investigated.

Therefore, there is a significant need for the development of strategies to prevent or delay MuSCs senescence in order to facilitate muscle regeneration after injury or be used in diseases related to impair MuSCs function and in aging.

SUMMARY OF THE INVENTION

The present invention is directed to the unexpected findings that the induction of the mitochondrial unfolded protein response (UPR$^{mt}$) and of prohibitin proteins can directly impact the regulation of muscle stem cell senescence. The induction of the mitochondrial unfolded protein response (UPR$^{mt}$) and specifically of prohibitin proteins by a mitochondrial UPR$^{mt}$ inducing agent such as nicotinamide riboside (NR) or thiamphenicol rejuvenates MuSCs in aged mice. Strategies that induce mitochondrial unfolded protein response (UPR$^{mt}$) and of prohibitin proteins could therefore be utilized to reprogram dysfunctional SCs in aging and disease to improve healthspan in mammals. One aspect of the invention provides a mitochondrial UPR$^{mt}$ inducing agent for use in the prevention and/or treatment of diseases or disorders associated with skeletal MuSCs senescence and/or for promoting muscle tissue growth and/or repair.

Another aspect of the invention provides a use of a mitochondrial UPR$^{mt}$ inducing agent for the preparation of a composition for prevention and/or treatment of diseases or disorders associated with skeletal MuSCs senescence and/or for promoting muscle tissue growth and/or repair.

Next, aspect of the invention provides a composition comprising a mitochondrial UPR$^{mt}$ inducing agent and an agent useful in the prevention and/or treatment of diseases or disorders associated with skeletal MuSCs senescence and/or useful for promoting muscle tissue growth and/or repair.

Another aspect of the invention provides a muscle stem cell culture medium or a composition for preservation of muscle cells, muscle grafts and muscle tissues comprising a mitochondrial UPR$^{mt}$ inducing agent.

Another aspect of the invention provides a method of preventing and/or treating of diseases or disorders associated with skeletal MuSCs senescence and/or promoting muscle tissue growth and/or repair in a subject, said method comprising administering an effective amount of a mitochondrial UPR$^{mt}$ inducing agent or a pharmaceutical composition thereof in a subject.

Another aspect of the invention provides a method of in vivo maintaining and/or extending sternness of skeletal muscle stem cell population comprising contacting a skeletal muscle stem cell population or a muscle stem cell containing sample with a composition of the invention.

Another aspect of the invention provides a method for promoting muscle tissue growth and/or repair, in particular for improving muscle cell/tissue survival, comprising using a composition or a method of the invention.

Another aspect of the invention provides an ex-vivo method for preparing a muscle graft sample in view of promoting muscle tissue growth and/or repair, in particular for improving cell/tissue survival after grafting said graft sample.

A further aspect of the invention provides a kit for skeletal muscle stem cell culture or for preservation of muscle cells, samples or tissues comprising at least one mitochondrial UPR$^{mt}$ inducing agent or a composition of the invention with instructions of use.

Another aspect of the invention provides a method of cell-based therapy, said method comprising administering, grafting a skeletal muscle stem cell composition of the invention. Said skeletal muscle stem cells could be prepared according to a method of the invention.

DETAILED DESCRIPTION

Figure 1:
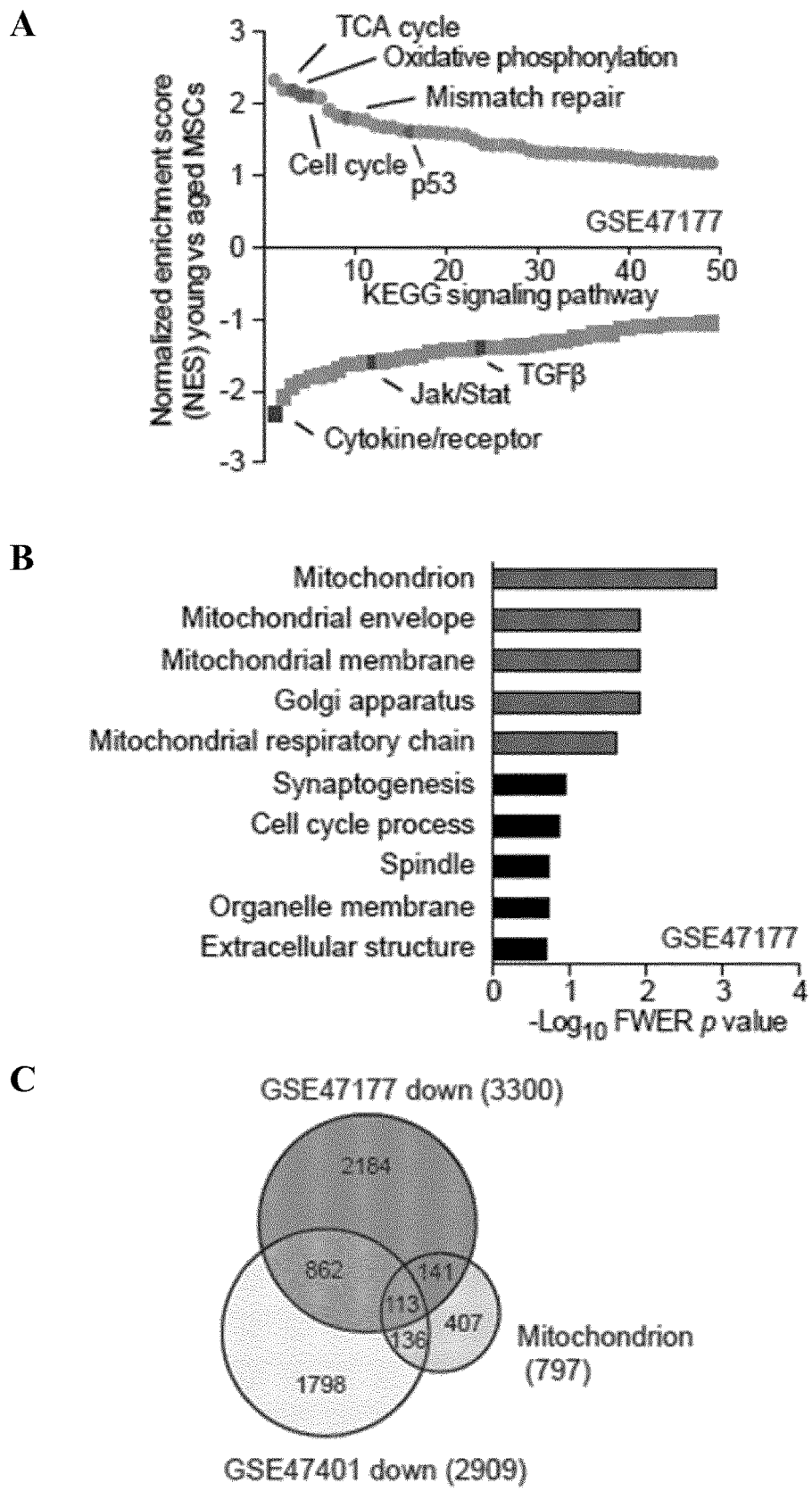
FIG. 1 shows reduction of mitochondrial content and oxidative respiration in MuSCs during aging. A: GSEA demonstrates up- and downregulated signaling pathways in MuSCs from two-year-old mice, compared to four-month-old mice. Signaling pathways are ranked on the basis of normalized enrichment scores (NESs); positive and negative NESs indicate down- or upregulation in aged MuSCs, respectively. Specific pathways related to MuSC function are marked in black. B: Top 10 ranked downregulated pathways in MuSCs from aged animals (GSE47177), based on gene ontology (GO) enrichment. Pathways are ranked by family wise error rate (FWER) p values. The top 5 significant down-regulated pathways are marked in grey. C: Area-proportional Venn diagram representing 113 common genes between the significantly downregulated genes (p<0.05) in MuSC transcriptomes originating from aged mice (GSE47177 and GSE47401), and genes from the human mitochondrial transcriptome. D: Pie chart illustrating the percent composition of the common 113 mitochondrial genes found in C. TXN, transcription, TLN, translation. E, Custom gene-set analysis showing enrichment of OXPHOS, TCA cycle and UPR$^{mt}$ related transcripts from MuSCs of young (Y) and aged (A) mice obtained from three independent data sets (GSE47177, GSE47401 and GSE47104). Roman numerals indicate corresponding OXPHOS complexes.
Figure 1:
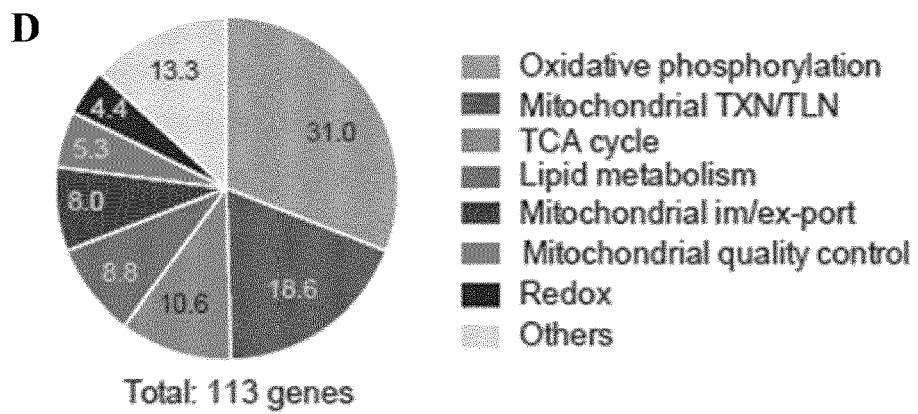
Figure 1:
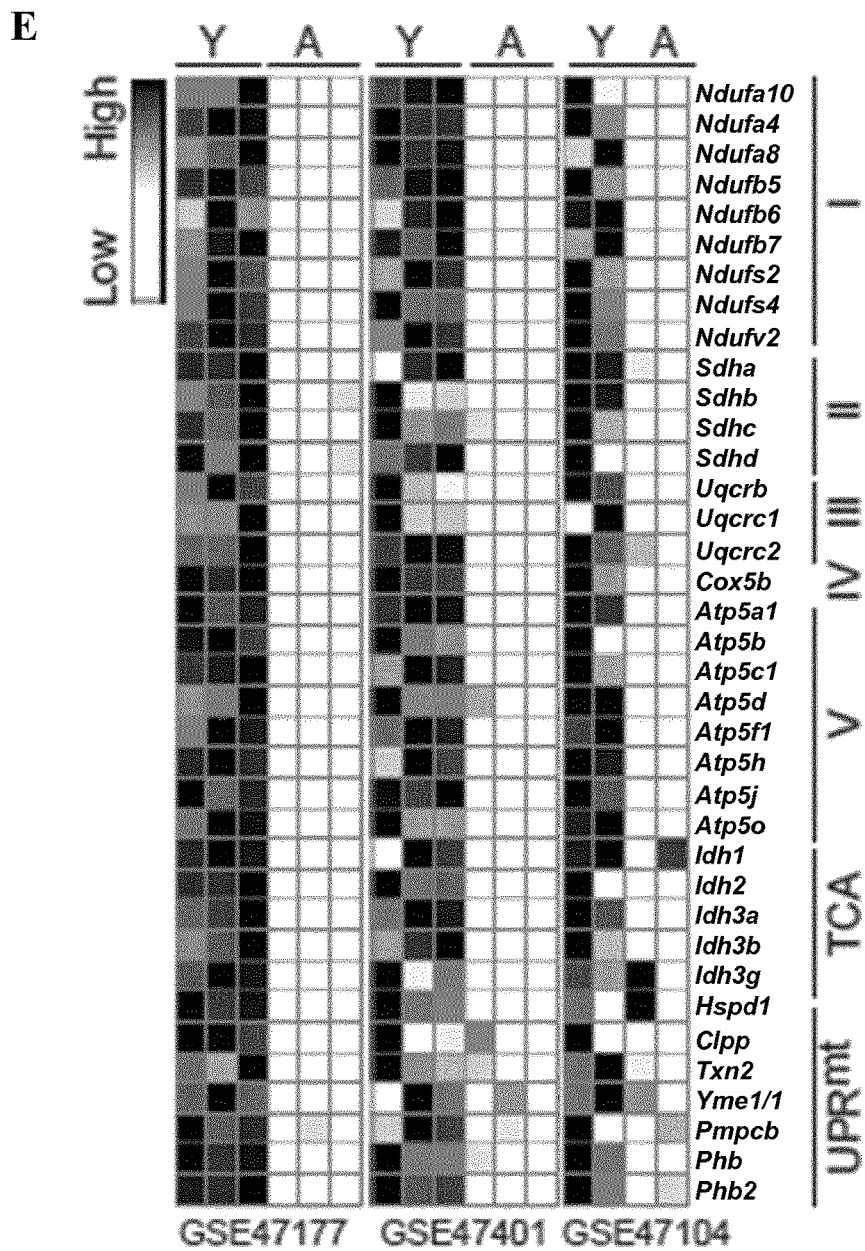

As used herein "adult stem cells" or "SCs" or "somatic stem cells" refers to undifferentiated cells, found throughout the body after development, capable of self-renewal (ability of multiply by cell division while still maintaining cell's undifferentiated state). The function of said cells is to replenish dying cells and regenerate damaged tissues of the organ from which they originate, potentially regenerating the entire organ from a few cells.

As used herein "muscle stem cells" or "MuSCs" or "satellite cells" that refers to adult stem cells of muscle, having the capacity to self-renew and to differentiate into myocytes, which fuse amongst each other or with the existing myofibers to compose the muscle fiber units. The known markers of MuSCs include, but are not limited to several transcription factors PAX7, MYF5 and cell surface antigens CD34, Integrin α7 and M-Cadherin (Yin et al., 2013, *Physiological Reviews*, 93: 23; Tabebordbar et al., 2013, *Annual Review of Pathology*, 8: 441).

As used herein "SC senescence" refers to a stable and irreversible loss of proliferative capacity (stable cell cycle arrest), despite continued viability and metabolic activity. Specific markers of MuSCs senescence include, among others, β-galactosidase activation, H2γAX phosphorylation, downregulation of cell cycle regulators (Mki67, Cdk4, Ccnd1, Cdkn1a), and induction of inflammatory factors (IL6 and IL18) (Kuilman et al., supra; Lopez-Otin et al., supra). Cdkn1a and Cdkn2a are among the most important general regulators of cellular senescence that are increased in senescent muscle SCs (Burd et al., supra; Lopez-Otin et al., supra).

The expression "skeletal muscle stem cell senescence" includes muscle dystrophy diseases, includes Duchenne's muscular dystrophy (DMD), Becker's muscular dystrophy (BMD), Congenital muscular dystrophy, Distal muscular dystrophy, Emery-Dreifuss' muscular dystrophy, Facio-scapulo-humeral muscular dystrophy, Limb-girdle muscular dystrophy, Myotonic muscular dystrophy and Oculopharyngeal muscular dystrophy. It further includes other inherited myopathies, such as myotonia, congenital myopathies (includes nemaline myopathy, multi/minicore myopathy, centronuclear myopathy), metabolic myopathies (includes glycogen storage diseases and lipid storage disorder), inflammatory myopathies, such as dermatomyositis, polymyositis, inclusion body myositis and auto-immune myositis. Other diseases linked to muscle stem cell senescence include muscle wasting induced by nutritional deficiencies. Diseases linked to muscle stem cell senescence may be developed in the context of other diseases, such as chronic obstructive pulmonary disease (COPD), chronic inflammatory syndromes, and cachexia of cancer. Further, diseases linked to muscle stem cell senescence may be developed as a result of clinical treatments that use compounds such as anthracyclines (i.e. doxorubicin) that can cause severe skeletal muscle and cardiac muscle toxicity leading to heart failure (Piegari et al., 2013, *Basic Res Cardiol.* 108(2): 334).

According to a particular aspect, muscle stem cells and muscle stem cell-containing samples for graft purposes are allogeneic and autologous.

The term "cell-based therapy" or "cell-based tissue regeneration" include cell replacement therapies making use of allogenic or autologous muscle stem cells, or in the direct induction of tissue regeneration by in situ stimulation of resident muscle stem cells (e.g. inducing resident stem cells mobilization and differentiation for repair), as alternatives to surgical interventions and muscle organ/tissue transplantation. Methods and compositions according to invention can be advantageously used in methods of "cell-based therapy" or "cell-based tissue regeneration" methods used to produce differentiated muscle tissue from progenitor cells or stem cells.

As used herein the term "skeletal muscle stem cell (MuSC) sample" or "muscle stem cell (MuSC) containing sample" comprises any ex-vivo sample comprising muscle stem cell isolated from a source of said cells (e.g. human or mouse skeletal muscle tissue). As used herein, the term "muscle stem cell culture medium" refers to any standard cell stem cell culture medium, optionally comprising appropriate differentiation factors, the nature of which may be adapted to the nature of the cell, in particular culture medium suitable for stem cell expansion such as for example culture media described in the following examples or described in Boitano et al., 2010, *Science* 329,1345-8.

According to a particular aspect, the medium for isolation and maintenance of muscle cells or muscle tissues according to the invention may further comprise of fetal bovine serum (FBS), recombinant human basic fibroblast growth factor (rhFGF), or chicken embryo extract, penicillin and streptomycin.

As used herein, the term "mitochondrial $UPR^{mt}$ inducing agent" is an agent which is able to induce $UPR^{mt}$ such as measured by several $UPR^{mt}$ markers including HSP60, CLPP, HSP70/Mortalin and prohibitins.

Mitochondrial $UPR^{mt}$ inducing agent can be easily identified by known techniques, such via monitoring the induction of CLPP, HSP60, HSP70/Mortalin, or prohibitins proteins, the imbalance between proteins encoded in mtDNA or nDNA, the induction of cellular $NAD^+$ contents, and the reduction of cellular PARylation status. Examples of said agent include, but are not limited nicotinamide riboside (NR), thiamphenicol, or thiamphenicol analogs thereof such as amphenicols. According to another aspect, mitochondrial $UPR^{mt}$ inducing agents are tetracyclines or analogues thereof. Identification of any further agents to able to induce $UPR^{mt}$ can be identified by standard methods known to the skilled person.

As used herein, the term "thiamphenicol analogs" includes amphenicols such as chloramphenicol. Amphenicols are antibiotics with a phenylpropanoid structure such as chloramphenicol, azidamfenicol and florfenicol.

As used therein, the term "tetracyclines" includes doxocycline and minocycline.

As used herein, the term "MuSCs cell depleted subjects" mean subjects presenting a significant reduction in the quantity and quality of muscle tissue specific adult muscle stem cells and more specifically aged human subjects, MuSCs are reduced.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it for example based on familial history or age; (b) inhibiting the disease, i.e., arresting its development; or relieving the disease, i.e., causing regression of the disease and/or its symptoms or conditions such as improvement or remediation of damage. In particular, a method according to the invention is useful in the maintenance and/or extension of stemness of stem cell population; prevention of cell senescence/apoptosis of stem cell population; maintenance and/or prevention of the reduction of stem cell proliferation/cell cycle process; maintenance and or prevention of the reduction of differentiation potential of stem cell population.

The term "subject" as used herein refers to mammals. For example, mammals contemplated by the present invention include human, primates, domesticated animals such as dogs, cats, cattle, sheep, pigs, horses, laboratory rodents and the like.

The term "efficacy" of a treatment or method according to the invention can be measured based on changes in the course of disease or condition in response to a use or a method according to the invention. For example, the efficacy of a treatment or method according to the invention can be measured through the measurement of through the measurement of muscle damage parameters from blood biochemical measurements of creatine kinase, aspartate aminotransferase and total protein levels. The efficacy of a treatment or method according to the invention can be measured through the measurement of muscle force, as well as immunostaining of MuSCs number and the analysis of regeneration of damaged muscle.

The terms "effective amount", "therapeutic effective amount", and "prophylactic effective amount" refer to a dosage of a compound or composition effective for eliciting a desired effect, commensurate with a reasonable benefit/risk ratio and will vary from subject to subject, depending, for example, on species, age, and general condition of a subject, severity of the side effects or disorder, identity of the particular compound(s), mode of administration, and the like. In certain embodiments, the desired dosage can be delivered using multiple administrations. Those terms as used herein may also refer to an amount effective at bringing about a desired in vivo effect in an animal, preferably, a human, such as induction of proliferation of tissue specific stem cells and the acceleration of tissue regeneration.

The efficacy of a treatment or method according to the invention can be measured by determining the level of cell maturation or of cell differentiation in the cell culture medium using standard methods in the art, including visual observation by microscopy, detection of markers which are specific for the targeted differentiated tissue by immunological staining or blotting and by molecular assays of mRNA, chromatin, nuclear DNA, mtDNA, or microRNA.

Use According to the Invention

According to an embodiment, the invention provides a mitochondrial UPR$^{mt}$ inducing agent for use in the prevention and/or treatment of a disease or disorder associated with muscle SC senescence and/or decreased muscle SCs number and/or for promoting muscle tissue growth and/or repair.

According to another embodiment, the invention provides a use of a mitochondrial UPR$^{mt}$ inducing agent for the preparation of a composition or a food supplement for the prevention and/or treatment of a disease or disorder associated with associated with muscle SC senescence and/or decreased muscle SCs number and/or for promoting muscle tissue growth and/or repair.

According to another embodiment, the invention provides a mitochondrial UPR$^{mt}$ inducing agent or composition thereof for use in the treatment of an injured muscle tissue notably after an injury or trauma.

According to another embodiment, the invention provides a method for promoting tissue growth and/or repair, in particular for improving cell/tissue survival, said method comprising contacting or administering to a muscle stem cell or to an isolated muscle tissue in culture before transplantation/grafting to a mammal in need thereof (ex-vivo), a mitochondrial UPR$^{mt}$ inducing agent or composition thereof in an amount effective to stimulate differentiation, maturation, proliferation, survival of cells and tissues and/or maintain and/or extend stemness of stem cell population.

A method of preparation of a cell composition for cell-based therapy comprising a step of contacting with or administering to a muscle stem cell a mitochondrial UPR$^{mt}$ inducing agent or composition thereof.

According to a further embodiment of the invention, is provided a kit for muscle stem cell culture or muscle tissue graft preparation or preservation comprising at least one mitochondrial UPR$^{mt}$ inducing agent or mixtures of formulations thereof together with instructions for use.

A method of preparation of a graft organ, cell or tissue comprising a step of contacting said graft organ, cell or tissue with a mitochondrial UPR$^{mt}$ inducing agent or composition thereof.

According to a further embodiment, the invention provides a method of prevention and/or treatment of diseases or disorders associated with muscle SC senescence, said method comprising grafting of a cell composition or graft sample prepared according to methods described herein.

According to a particular embodiment, the invention provides a method for promoting muscle tissue growth and/or repair in a subject in need thereof, said method comprising administering an effective amount of a mitochondrial UPR$^{mt}$ inducing agent or composition thereof in said subject.

According to a particular aspect, a disease or disorder associated with muscle SC senescence and/or decreased muscle SCs number is selected from muscle dystrophies, myopathies and muscle frailty and sarcopenia of the aged.

According to a particular aspect, a method of the invention is an ex-vivo method useful for maintaining and/or extending stemness of a muscle stem cell population.

According to another particular embodiment of the invention, is provided a method for ex-vivo preparing a graft sample comprising the steps of:
a) providing a MuSC-containing sample in a stem cell culture medium;
b) contacting said MuSC-containing sample with at least one mitochondrial UPR$^{mt}$ inducing agent or a mixture thereof in an amount effective to stimulate the survival and the maintenance of the stemness of the stem cells within the sample increased as compared to a sample in absence of said mitochondrial UPR$^{mt}$ inducing agent.

According to a further aspect, said MuSC-containing sample is further combined with a muscle tissue or organ to be grafted, before grafting. Isolated muscle stem cells can be treated with at least one UPR$^{mt}$ inducing agent or a mixture thereof, or in combination with another agent useful to proliferation and maintenance of stemness.

According to a particular aspect, the method of muscle graft sample preparation of the invention is useful for promoting muscle tissue growth and/or repair following graft sample grafting.

According to another particular embodiment, is provided an ex-vivo method of the invention wherein stemness (e.g. self-renewing capacity of SCs) is assessed by quantifying stemness markers such as transcription factors PAX7, MYF5 and cell surface antigens CD34, Integrin α7 and M-Cadherin of the cell preparation obtained after step b).

According to another embodiment, is provided a muscle stem cell culture medium comprising at least one mitochondrial UPR$^{mt}$ inducing agent, optionally further comprising a cocktail of cytokines and growth factors useful for stem cell expansion.

According to a further embodiment, the agent mitochondrial UPR$^{mt}$ inducing agent is selected from NR, thiamphenicol or analogues thereof, such as amphenicols. According to another further embodiment, the mitochondrial UPR$^{mt}$ inducing agent is NR.

According to another further embodiment, the mitochondrial UPR$^{mt}$ inducing agent is thiamphenicol or an analogue thereof.

According to another further embodiment, the mitochondrial UPR$^{mt}$ inducing agent is a tetracycline or an analogue thereof.

In particular, treatment of diseases or disorders associated with MuSC senescence comprises promoting tissue homeostasis, tissue regeneration, and the ability of stem cells to infiltrate tissues upon transplantation. This includes maintenance and/or extension of stemness of stem cell population; maintenance and/or prevention of the reduction of stem cell proliferation/cell cycle process; maintenance and/or prevention of the reduction of differentiation potential of stem cell population.

Muscle cells and muscle graft samples obtained by a method according to the invention can be formulated for clinical stem cell or graft or tissue transplantation, or for augmentation stem function or for cell-based therapy in a subject in need thereof.

Compositions According to the Invention

Mitochondrial UPR$^{mt}$ inducing agent or formulations thereof may be administered as a pharmaceutical formulation or a food supplement or may be formulated as stem cell culture or organ preservation media, which can contain one or more agents according to the invention in any form described herein. The compositions according to the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use by injection or continuous infusion. Injectable compositions are typically based upon injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Compositions of this invention may be liquid formulations including, but not limited to, aqueous or oily suspensions, solutions, emulsions, syrups, and elixirs. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methylcellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Compositions of this invention may also be formulated as a depot preparation, which may be administered by implantation or by intramuscular injection.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maize starch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate.

Tablets may be coated according to methods well known in the art.

The compounds of this invention can also be administered in sustained release forms or from sustained release drug delivery systems.

According to a particular embodiment, compositions according to the invention are for intravenous use.

According to a particular aspect, the formulations of the invention are oral formulations.

According to a particular embodiment, compositions according to the invention are food supplement.

In another particular aspect, the compositions according to the invention are adapted for delivery by repeated administration.

In another particular aspect, the compositions according to the invention are adapted for the stem cell culture or graft preparation or transplantation.

According to a particular embodiment, compositions of the invention are veterinary compositions.

According to a particular embodiment, compositions of the invention are adapted for topical delivery.

Further materials as well as formulation processing techniques and the like are set out in Part 5 of Remington's "The Science and Practice of Pharmacy", 22$^{nd}$ Edition, 2012, University of the Sciences in Philadelphia, Lippincott Williams & Wilkins, which is incorporated herein by reference.

Mode of Administration

Mitochondrial UPR$^{mt}$ inducing agents or formulations thereof may be administered in any manner including orally, parenterally, intravenously, rectally, or combinations thereof. Parenteral administration includes, but is not limited to, intravenous, intra-arterial, intra-peritoneal, subcutaneous and intramuscular. The compositions of this invention may also be administered in the form of an implant, which allows slow release of the compositions as well as a slow controlled iv infusion.

According to a particular aspect, mitochondrial UPR$^{mt}$ inducing agents or formulations thereof are to be administered by injection.

According to a particular aspect, the mitochondrial UPR$^{mt}$ inducing agent or formulation thereof are to be administered orally.

Typically, a dosage rate of NR can be at a dosage rate ranging from about 1 mg/kg/day to about 400 mg/kg/day.

Typically, a dosage rate of thiamphenicol can be at a dosage rate ranging from about 5 to about 15 mg/kg/day.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Combination

According to the invention, mitochondrial UPR$^{mt}$ inducing agents or formulations thereof, including pharmaceutical formulations thereof can be administered alone or in combination with a co-agent (e.g. multiple drug regimens) useful for preventing or treating a disease or disorder associated with muscle SC senescence and/or decreased muscle SCs number.

According to the invention, mitochondrial UPR$^{mt}$ inducing agents or formulations thereof, including pharmaceutical formulations thereof can be administered alone or in combination with a co-agent (e.g. multiple drug regimens) useful for graft muscle tissue improvement, in particular for promoting muscle tissue growth and/or repair, in particular for improving cell/tissue survival.

According to the invention, mitochondrial UPR$^{mt}$ inducing agents or formulations thereof, can be administered to a subject prior to, simultaneously or sequentially with other therapeutic regimens or co-agents useful for preventing or treating a disease or disorder associated with muscle SC senescence and/or decreased muscle SCs number or useful for promoting muscle tissue growth and/or repair.

A compound of the invention or a formulation thereof according to the invention that is administered simultaneously with said co-agents can be administered in the same or different composition(s) and by the same or different route(s) of administration.

According to a particular embodiment, is provided a formulation (such as a food supplement or a pharmaceutical composition) comprising a mitochondrial UPR$^{mt}$ inducing agent, combined with at least one co-agent useful for preventing or treating a disease or disorder associated with muscle SC senescence and/or decreased SCs number or useful for promoting muscle tissue growth and/or repair. These co-agents include but are not limited to transforming growth factor β (TGFβ) family protein/receptor inhibitors, such as the myostatin inhibitor or follistatin-derived peptide FS I-I (Tsuchida, 2008, Acta Myol, 27(1):14-18), P38 and JAK-STAT signalling pathway inhibitors, including compounds such as SB203580, SB202190, BIRB796, AG490, 5,15-Diphenylporphyrin (Bernet et al., supra; Cosgrove et al., supra; Price et al., supra); muscle stem cell activators, such as Notch signalling activators (Conboy et al., 2005, *Nature*, 433:760) and anabolic stimulators of the muscle, such as IGF-1 (Musaro, et al., 2004, *Basic Appl Myol*, 14(1):29-32).

Patients

According to an embodiment, subjects according to the invention are subjects suffering from disease or disorders associated with muscle stem cells senescence, in particular stem cell related muscular dystrophy, such as Duchenne's muscular dystrophy (DMD), Becker's muscular dystrophy (BMD), Congenital muscular dystrophy, Distal muscular dystrophy, Emery-Dreifuss' muscular dystrophy, Facio-scapulo-humeral muscular dystrophy, Limb-girdle muscular dystrophy, Myotonic muscular dystrophy and Oculopharyngeal muscular dystrophy.

In another particular embodiment, subjects according to the invention are subjects suffering from disease or disorders associated with muscle stem cells senescence, in particular inherited myopathies that includes diseases such as myotonia, congenital myopathies such as nemaline myopathy, multi/minicore myopathy and centronuclear myopathy, metabolic myopathies such as glycogen storage diseases and lipid storage disorder, inflammatory myopathies, such as dermatomyositis, polymyositis, inclusion body myositis and auto-immune myositis.

In another particular embodiment, subjects according to the invention are subjects suffering from non-mitochondrial myopathies.

In a particular embodiment, subjects according to the invention are subjects suffering from disease or disorders associated with muscle stem cells senescence resulting from a traumatic injury.

In a particular embodiment, subjects according to the invention are subjects suffering from disease or disorders associated with muscle stem cells senescence in frailty and sarcopenia, resulting from aging.

In another particular embodiment, subjects according to the invention are muscle stem cells depleted subjects, in particular aged subjects.

In another particular embodiment, subjects according to the invention are subjects suffering from disease or disorders associated with muscle stem cells senescence, in particular muscle wasting induced by nutritional deficiencies.

In another particular embodiment, subjects according to the invention are subjects suffering from disease or disorders associated with muscle stem cells senescence, in particular developed in the context of diseases, such as chronic obstructive pulmonary disease (COPD), chronic inflammatory syndromes, and cachexia of cancer.

In another particular embodiment, subjects according to the invention are subjects suffering from disease or disorders associated with muscle stem cells senescence, in particular acquired myopathies, such as drug/toxic agents-induced myopathy, alcoholic myopathy, myositis ossificans, rhabdomyolysis and myoglobinurias.

In an embodiment, subjects according to the invention are subjects undergoing graft transplantation.

References cited herein are hereby incorporated by reference in their entirety. The present invention is not to be limited in scope by the specific embodiments and drawings described herein, which are intended as single illustrations of individual aspects of the invention, and functionally equivalent methods and components are within the scope of the invention. The examples illustrating the invention are not intended to limit the scope of the invention in any way.

EXAMPLES

CASP3 (caspase-3), Cdkn1a (cyclin-dependent kinase inhibitor 1A or p21), CTX (cardiotoxin), DAPI (4',6-diamidino-2-phenylindole), eMyHC (embryonic myosin heavy chain), GO (gene ontology), GSEA (gene set enrichment analysis), OCR (oxygen consumption rate), OXPHOS (oxidative phosphorylation), $UPR^{mt}$ (mitochondrial unfolded protein response), NES (normalized enrichment scores), NR (nicotinamide riboside), TCA (tricarboxylic acid cycle), TA (tibialis anterior).

Example 1

Identification of Mitochondrial Dysfunction as a Biomarker of MuSCs Senescence

To identify the role of mitochondrial function in muscle SCs senescence, MuSCs from young and aged mice were compared. To identify the principal mechanisms initiating MuSC senescence, publically available MuSC gene expression datasets from young (~3 months) and aged (~24 months) mice were compared with the use of gene set enrichment analysis. (GSEA; GEO dataset IDs: GSE47177, GSE47401 and GSE47104) as described below.

Bioinformatic analysis. Quadriceps microarray data from young and aged mice MuSCs (Price et al., supra; Bernet et al., supra; Liu et al., supra) were analyzed for transcript expression using the Kyoto encyclopedia of genes and genomes (KEGG), gene ontology (GO) or gene set enrichment analysis (GSEA) analysis. Raw microarray data are also publicly available on Gene Expression Omnibus (GEO) database under the accession numbers GSE47177, GSE47401 and GSE47104. All gene expression heat maps were draw using GENE-E software.

Gene expression analyses. Total RNA was extracted from MuSCs by sorting cells directly into TriPure RNA isolation reagent (Roche) or from cultured C2C12 myoblasts using TriPure reagent according to the product manual. Total RNA was transcribed to cDNA using QuantiTect Reverse Transcription Kit (Qiagen). Expression of selected genes was analyzed using the LightCycler480 system (Roche) and LightCycler® 480 SYBR Green I Master reagent (Roche). The acidic ribosomal protein 36b4 gene (ribosomal protein, large, P0, Rp1p0) was used as housekeeping reference. Primer sets for quantitative real-time PCR analyses are shown in Table 1 below.

TABLE 1

| Gene name | Forward primer | Reverse Primer |
|---|---|---|
| 36b4 | AGATTCGGGATATGCTGTTGG SEQ ID NO: 1 | AAAGCCTGGAAGAAGGAGGTC SEQ ID NO: 2 |

TABLE 1-continued

| Gene name | Forward primer | Reverse Primer |
|---|---|---|
| Ndufb5 | CTTCGAACTTCCTGCTCCTT SEQ ID NO: 3 | GGCCCTGAAAAGAACTACG SEQ ID NO: 4 |
| Sdha | GGAACACTCCAAAAACAGACCT SEQ ID NO: 5 | CCACCACTGGGTATTGAGTAGAA SEQ ID NO: 6 |
| Sdhc | GCTGCGTTCTTGCTGAGACA SEQ ID NO: 7 | ATCTCCTCCTTAGCTGTGGTT SEQ ID NO: 8 |
| Cox5b | AAGTGCATCTGCTTGTCTCG SEQ ID NO: 9 | GTCTTCCTTGGTGCCTGAAG SEQ ID NO: 10 |
| Atp5b | GGTTCATCCTGCCAGAGACTA SEQ ID NO: 11 | AATCCCTCATCGAACTGGACG SEQ ID NO: 12 |
| Mdh2 | TTGGGCAACCCCTTTCACTC SEQ ID NO: 13 | GCCTTTCACATTTGCTCTGGTC SEQ ID NO: 14 |
| Idh2 | GGAGAAGCCGGTAGTGGAGAT SEQ ID NO: 15 | GGTCTGGTCACGGTTTGGAA SEQ ID NO: 16 |
| Idh3a | CCCATCCCAGTTTGATGTTC SEQ ID NO: 17 | ACCGATTCAAAGATGGCAAC SEQ ID NO: 18 |
| Cdkn1a | GTGGGTCTGACTCCAGCCC SEQ ID NO: 19 | CCTTCTCGTGAGACGCTTAC SEQ ID NO: 20 |
| Mki67 | TTGGAAAGGAACCATCAAGG SEQ ID NO: 21 | TTTCTGCCAGTGTGCTGTTC SEQ ID NO: 22 |
| Cdk4 | CCGGTTGAGACCATTAAGGA SEQ ID NO: 23 | CACGGGTGTTGCGTATGTAG SEQ ID NO: 24 |
| Ccna2 | AAGAGAATGTCAACCCCGAAA SEQ ID NO: 25 | ACCCGTCGAGTCTTGAGCTT SEQ ID NO: 26 |
| Ccnd1 | GAGCGTGGTGGCTGCGATGCAA SEQ ID NO: 27 | GGCTTGACTCCAGAAGGGCTTCAAT SEQ ID NO: 28 |
| Ccne1 | CAAAGCCCAAGCAAAGAAAG SEQ ID NO: 29 | CCACTGTCTTTGGAGGCAAT SEQ ID NO: 30 |
| Cdc6 | GACACAAGCTACCATGGTTT SEQ ID NO: 31 | CAGGCTGGACGTTTCTAAGTT SEQ ID NO: 32 |
| IL6 | GGTGACAACCACGGCCTTCCC SEQ ID NO: 33 | AAGCCTCCGACTTGTGAAGTGGT SEQ ID NO: 34 |
| IL18 | GTGAACCCCAGACCAGACTG SEQ ID NO: 35 | CCTGGAACACGTTTCTGAAAGA SEQ ID NO: 36 |
| Hsp60 | ACAGTCCTTCGCCAGATGAGAC SEQ ID NO: 37 | TGGATTAGCCCCTTTGCTGA SEQ ID NO: 38 |
| Hsp10 | CTGACAGGTTCAATCTCTCCAC SEQ ID NO: 39 | AGGTGGCATTATGCTTCCAG SEQ ID NO: 40 |
| Clpp | CACACCAAGCAGAGCCTACA SEQ ID NO: 41 | TCCAAGATGCCAAACTCTTG SEQ ID NO: 42 |
| Phb | TCGGGAAGGAGTTCACAGAG SEQ ID NO: 43 | CAGCCTTTTCCACCACAAAT SEQ ID NO: 44 |
| Phb2 | CAAGGACTTCAGCCTCATCC SEQ ID NO: 45 | GCCACTTGCTTGGCTTCTAC SEQ ID NO: 46 |

Animals. Young (1 month old) and aged (20-24 months old) C57BL/6JRj mice, purchased from Janvier Labs, and five weeks old male C57BL/10SnJ mice or C57BL/10ScSn-Dmdmdx/J, purchased from The Jackson Laboratory, were fed with pellets containing vehicle or NR (400 mg/kg/day) for 6-8 weeks. The pellets were prepared by mixing powdered chow diet (D12450B, Research Diets Inc.) with water or with NR dissolved in water. Pellets were dried under a laminar flow hood for 48 hours. All mice were housed in micro-isolator cages in a room illuminated from 7:00 am -7:00 pm with ad libitum access to diet and water.

FACS based muscle stem cell isolation. Gastrocnemius, soleus, quadriceps, and tibialis anterior muscles from both limbs were excised and transferred into PBS on ice. All muscles were trimmed, minced and digested with 0.1 mg/ml of type II collagenase (Sigma) in PBS for 15 min at 37° C. Samples were then centrifuged at 750 g for 5 min and further digested in 1 mg/ml of collagenase/dispase (Roche) for 30 mins at 37° C. Muscle slurries were sequentially filtered through 100, 70 and 40 µm cell strainers. The isolated cells were then washed in washing buffer (PBS+2.5% FBS) then resuspended in 200 µl of washing buffer and immediately stained with antibodies, including the MuSC markers CD31 (1:800, eBioscience, eFluor450 conjugated); CD34 (1:200, eBioscience, eFluor660 conjugated); CD45 (1:200, eBioscience, eFluor450 conjugated); CD11b (1:400, eBioscience, eFluor450 conjugated); Sca-1 (1:1000, eBioscience, PE-Cy7 conjugated); and α7 integrin (1:300, MBL) for 30 min at 4° C. Secondary staining was performed with a mixture of goat anti-mouse antibody (1:800, Life technologies, Alexa Fluor 488 conjugated) and propidium Iodide (PI, Sigma) for 15 min at 4° C. in the dark. Stained cells were analysed and sorted using the FACSAria II instrument (BD Biosciences). Debris and dead cells were excluded by forward scatter, side scatter and PI gating. Cells were sorted either directly on slides for immunostaining and into TriPure (Roche) reagent for RNA extraction.

Respirometry on MuSCs. Basal and uncoupled oxygen consumption rates (OCRs) were measured using the Seahorse extracellular flux bioanalyzer (XF96, Seahorse Bioscience Inc.). To uncouple mitochondria, 5 uM of FCCP was injected after a basal respiration measurement. All measurements were performed in triplicates and results were normalized to total cell number seeded (primary MuSCs) assessed using a Bradford kit (Bio-Rad).

Enrichment scores of young versus aged datasets demonstrate the upregulation of senescence pathways and downregulation of cell cycle pathways with age (FIG. 1A) that is consistent with the paradigm that irreversible cell cycle arrest is a primary marker of cellular senescence (Kuilman et al., supra; Lopez-Otin et al., supra). In all three datasets, citric acid cycle (TCA, also known as the tricarboxylic acid cycle or the Krebs cycle) and oxidative phosphorylation (OXPHOS) pathways were amongst the most downregulated pathways in aged MuSCs, despite the general assumption that MuSCs predominantly rely on glycolysis (FIG. 1A). Gene ontology (GO) term analysis, of genes significantly (p<0.05) downregulated in aged MuSCs, further demonstrated that many of these pathways were related to mitochondrial function (FIG. 1B). Common downregulated genes during aging indicated a substantial overlap (113 genes; 11.59%) with mitochondrial genes (mitochondrial genes as in Mercer et al., 2011, Cell, 146: 645) (FIG. 1C) in contrast to the minimal (11 genes; 1.92%) overlap amongst common upregulated genes. Among the 113 downregulated mitochondrial genes in aged MuSCs, 41.6% were related to the TCA cycle and OXPHOS (FIG. 1D), which is significantly higher than their percent composition of the whole mitochondrial proteome (~14%) (Sickmann et al., 2003, PNAS, 100: 13207; Pagliarini et al., 2008, Cell, 134: 112). This indicates a dominant decline of mitochondrial respiratory genes in aged MuSCs. The reduction in mitochondrial OXPHOS and TCA cycle genes is consistent for all independent datasets (FIG. 1E).

Figure 2:
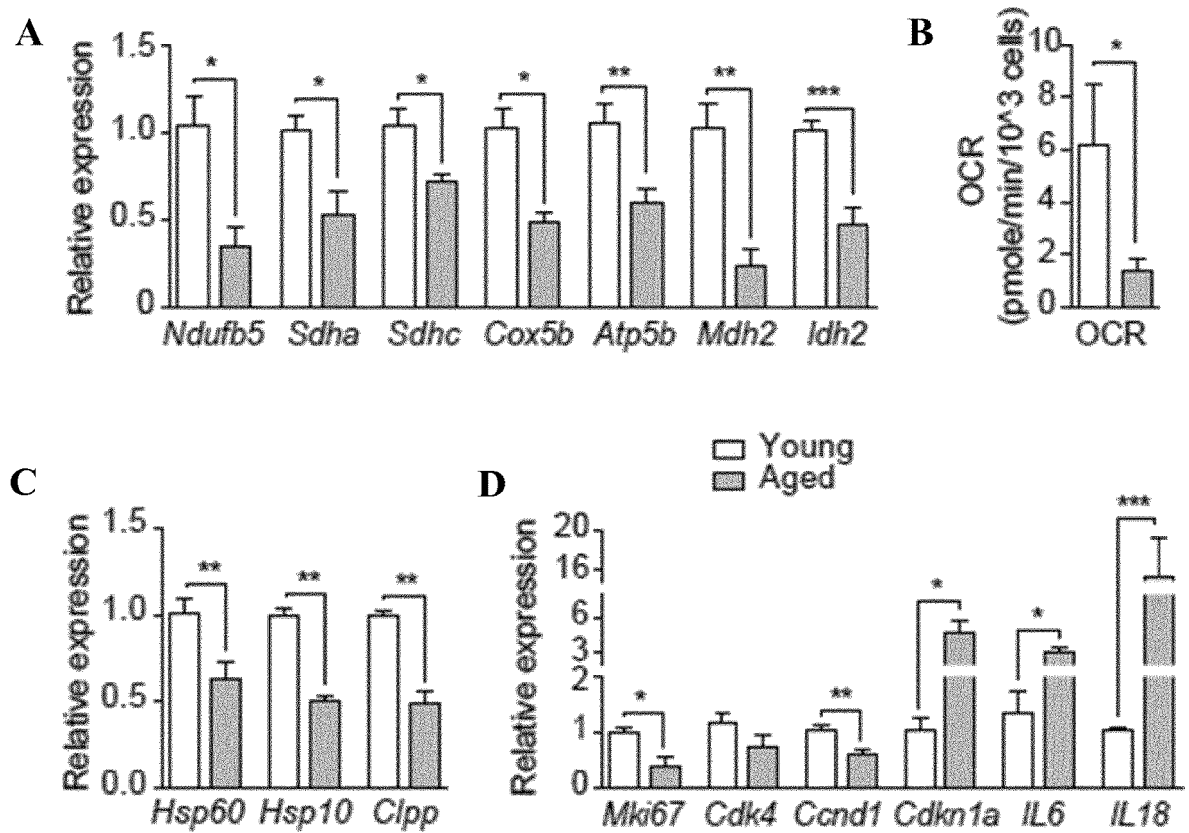
FIG. 2 shows reduction of mitochondrial content and oxidative respiration in MuSCs during aging. A-D: MuSCs were isolated from young (3 months old) and aged (22-24 months old) C57BL/6J mice either freshly (A, C and D) or under in vitro cell culture for three generations (B); A: qPCR validation of transcriptional changes in mitochondrial genes of freshly sorted MuSCs. B: OCR in isolated primary MuSCs, cultured in vitro for three generations. C-D: Relative gene expression for UPR$^{mt}$ genes (C) and cell senescence markers (D) in freshly sorted MuSCs. Data are normalized to 36b4 mRNA transcript levels. All data are shown as mean±s.e.m. A-D, n=6 mice per group. *P<0.05, **P<0.01. All statistical significance was calculated by Student's t test.

Confirming dysfunctional mitochondrial respiration, isolated primary aged and young MuSCs were isolated. Reductions in OXPHOS and TCA cycle transcripts were found (FIG. 2A), matched by a reduction in oxidative respiration rates (FIG. 2B). Interestingly, several important markers and regulators of the mitochondrial unfolded protein response ($UPR^{mt}$), a stress response pathway that mediates adaptations in mitochondrial content and function, were significantly downregulated in aged MuSCs (FIG. 1E and 2C, D). Notably, despite the absence of consistent changes in CDKN2A or MAPK14 (p38) pathways, previously reported to regulate MuSC senescence, there was a downregulation of cell cycle-related gene expression (FIG. 2D). The reduction in cell cycle signalling was accompanied by an upregulation of the cyclin-dependent kinase inhibitor 1A (CDKN1A)-mediated pathway (FIG. 2D), suggesting that early senescence in MuSCs may involve CDKN1A.

This data show that mitochondrial oxidative respiration is important for the functional maintenance of adult MuSCs during aging as a dominant decline mitochondrial OXPHOS and TCA cycle genes can be observed in aged MuSCs.

Example 2

NR Treatment Improves MuSCs Function in Aging Mice

The effect of a mitochondrial $UPR^{mt}$ inducing agent in the treatment of loss of MuSC numbers during aging was studied as follows:

Animals and FACS based muscle stem cell isolation as described in Example 1.

Endurance running test. Mice were fasted 2 hours before running on a treadmill. The exercise regimen commenced at a speed of 9 cm/s with an inclination of 5 degrees. The speed was gradually increased 3 cm/s every 12 minutes. Mice were considered to be exhausted, and removed from the treadmill, following the accumulation of 5 or more shocks (0.1 mA) per minute for two consecutive minutes. The distance traveled and time before exhaustion is registered as maximal running distance and period.

Grip strength test. Muscle strength was assessed by a grip strength behavior task. The grasp strength of each mouse for all four limbs was measured on a pull-grid assembly connected to a grip strength meter (Columbus Instruments). The mouse was drawn along a straight line parallel to the grid until the grip is broken, providing the peak force in grams. This was repeated 4 times with 5 minute intervals between measurements.

Cardiotoxin-induced muscle damage. Animals were anesthetized using Isoflurane in oxygen from a precision vaporizer. 50 µl of 20 µM Naje mossambica mossambica cardiotoxin (Sigma) was injected intramuscularly cross the skin and directly into the tibialis anterior (TA) muscle. Mice were sacrificed at 7 and 14 days after injury. TA muscles were immediately embedded in Thermo Scientific™ Shandon™ Cryomatrix™ and frozen in isopentane, cooled in liquid nitrogen, for 2 mins before being transferred to dry ice and stored at −80° C.

MuSCs transplantation. 5,000-8,000 double-sorted MuSCs isolated from NR or normal chow diet C57B/6J mice were resuspended in 10 µl of F10 media with 20% FBS and injected directly into cardiotoxin (CTX) pre-injured tibialis anterior (TA) muscle of Mdx mice 24hrs after the injury. The CTX pre-injury was performed as described above. Recipient mice were sacrificed 4 weeks after transplantation, TA muscle were harvested and prepared for cryosection.

Histology. TA muscles were harvested from anaesthetized mice and immediately frozen in Tissue-TEK® OCT compound (PST). 8-µm cryosections were collected and fixed with 4% paraformaldehyde, which are either stained with haematoxylin/eosin (HE) or antibodies. For immunostainings, heat activated antigen retrieval was performed in pH 6.0 citrate buffer for 10 min at 65° C. After washing with PBS-0.1% tween 20 (PBST), the sections were blocked with 10% affinipure Fab goat anti mouse IgG (Jackson Immunoresearch) in PBST for 60 min and PBST containing 2% BSA and 5% goat serum for 30 min at room temperature. Primary antibodies were then applied over night at 4° C. The following antibodies were used: anti-eMHC (Developmental Studies Hybridoma Bank, DSHB, University of Iowa), anti-Pax7 (DSHB, University of Iowa), anti-Laminin (Sigma). Subsequently, the slides were washed in PBST and incubated with appropriate secondary antibodies and labeling dyes. For immunofluorescence, secondary antibodies were coupled to Alexa-488 or Alexa-568 fluorochromes (Life technology), and nuclei were stained with DAPI (Invitrogen). After washing in PBST, tissue sections were mounted with Dako mounting medium (Dako).

Figure 3:
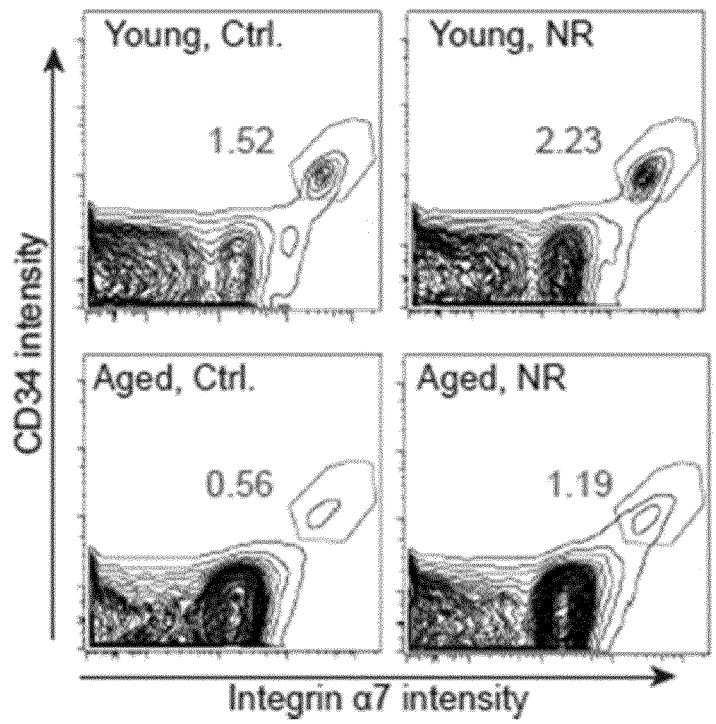
FIG. 3 shows improved muscle stem cell numbers and muscle function in NR-treated aged mice. Young (3 months old) and aged (22-26 months old) C57BL/6J mice received a dietary supplement with NR (400 mg/kg/day) for 6 weeks. All results are compared to age-matched mice given a control diet. A-C: FACS contour plots of Sca-1, Lin- (CD11b− CD23−, CD45−) cells isolated from muscle tissue. Percentage of the marker CD34+/integrin α7+/Lin-/Sca-1- cells, MuSC are noted in contour plots (A), and quantified relative to the total Lin-/Sca-1-cell population (B) or to the entire live cell population (C) for all treatment groups. D: Representative images of PAX7 immunostained (arrows) tibialis anterior (TA) muscle cross-sections from control and NR-treated aged mice. Arrows point to PAX7 positive SCs. 20×20 µm insets shows single MuSCs. Scale bar=50 µm. E-G: Comparison of maximal running distance (E), running period (F) and grip strength (G) between control and NR-treated aged mice. H: TA muscle structure in tissue-sections from NR-treated aged mice with 7 and 14 days of regeneration CTX induced muscle damage. Images show representative H/E staining of muscle cross sections. Scale bar=100 µm. I-J: Representative images (I) and quantification (J) of immunostained TA muscle cross-sections taken from control and NR-treated mice 7 days after CTX-induced muscle damage. Arrows point to PAX7 positive MuSCs. 20×20 µm insets show single MuSCs. Scale bar=50 µm. K: Quantification of the signal intensity ratio between MYOD1 and PAX7 in PAX7 positive muscle MuSCs, performed on sections isolated 7 days after muscle damage. L: Representative images of newly regenerated muscle fibers, indicated by eMyHC immunostaining (arrows), 7 days after muscle damage. Scale bar=50 µm. M: The schema of MuSCs transplantation experiments. MuSCs were double sorted from control and NR diet treated B6 mice and transplanted into the different hind limbs of the same Mdx mouse. N: Dystrophin immunostaining (arrows) of TA muscle sections in Mdx mice 4-weeks after receiving transplantations of MuSCs isolated from control or NR-treated aged C56BL/6J donors. Scale bar=100μm. All data are represented as mean±s.e.m. *p<0.05, p<0.01. *p<0.001. A-E and I-M, n=3-5 mice per group; F-H, n=10 control diet; n=7 NR-treated mice; N-O, n=12 donor mice, n=3 recipient mice for each treatment.
Figure 3:
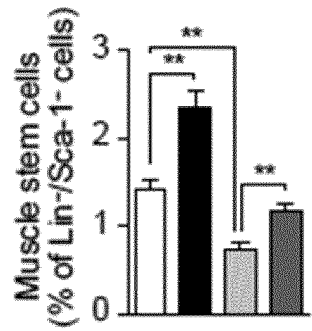
Figure 3:
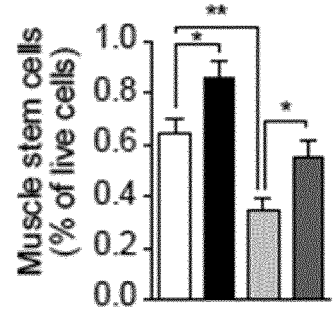
Figure 3:
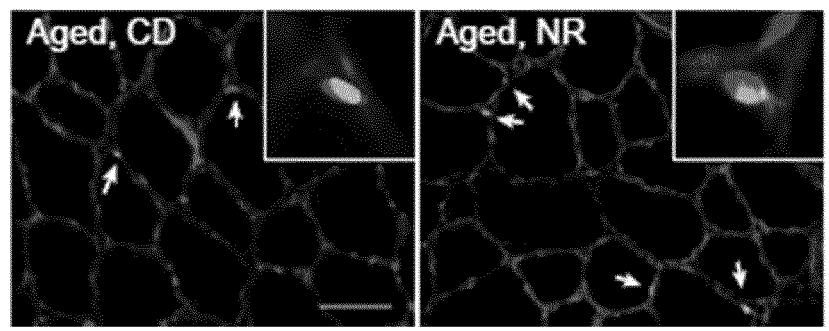
Figure 3:
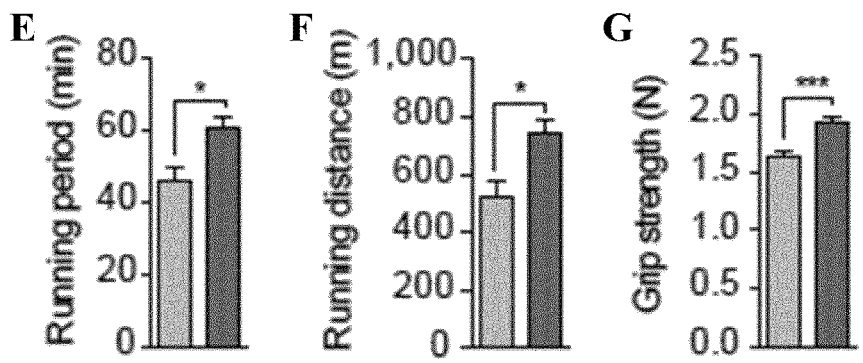
Figure 3:
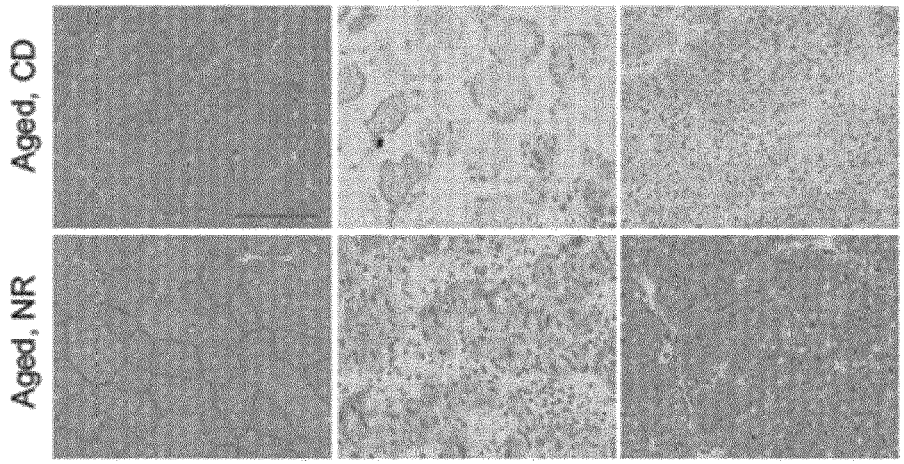
Figure 3:
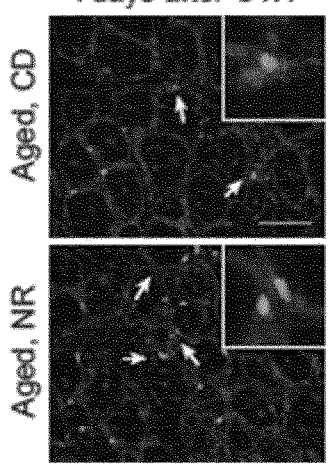
Figure 3:
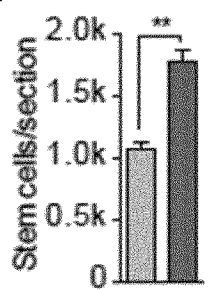
Figure 3:
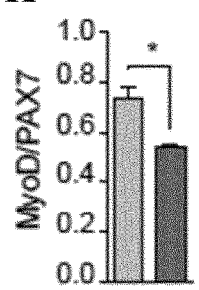
Figure 3:
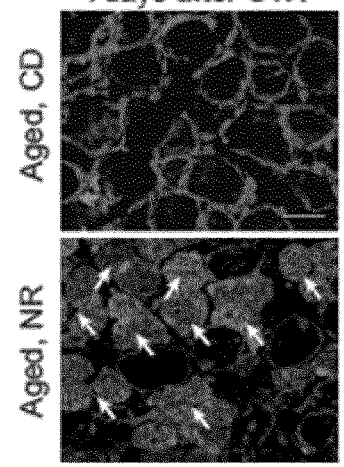
Figure 3:
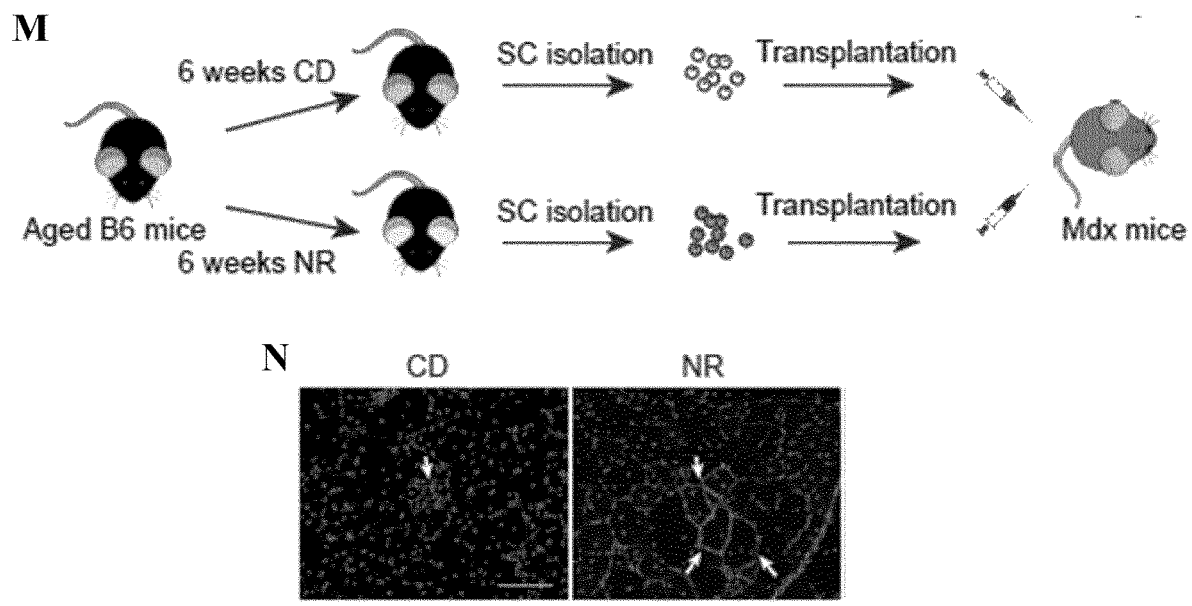

Compared to young, aged mouse muscle contained fewer MuSCs (FIG. 2A-C). However, nicotinamide riboside (NR) treatment attenuated the loss of MuSC numbers during aging, while also evoking gains in younger mice (FIG. 3 A-C). The increase in aged MuSC numbers was confirmed with PAX7 staining, a known MuSC marker (Yin et al., supra) (FIG. 3D). The effect of NR in young or aged mice was not due to changes in muscle mass or body weight, as they were comparable amongst all groups over this short treatment period. Consistent with the increase of MuSC numbers, NR treatment significantly enhanced muscle function as indicated by improvements in maximal running times and distances, along with limb grip strength (FIG. 3E-G). Impairments in muscle regeneration efficiency have been linked to the decline in aged MuSC function (Jang et al., supra). The action of NR on muscle regeneration with cardiotoxin (CTX)-induced muscle damage was tested (Yin et al., supra). Indeed, NR treatment accelerated muscle regeneration in aged and young mice (FIG. 3H). NR-induced improvements in regeneration were paralleled by increases in PAX7-positive MuSCs in aged mice (FIG. 3I-J), with a trend to increase in young mice. NR treatment also improved the stemness of the aged MuSCs, as demonstrated by a reduction in MYOD1-positive PAX7 immunostained cells, e.g. MuSCs started to differentiation (FIG. 3K). Complementing the improvements in MuSC function, 7 days after CTX-induced damage, NR-treated aged mice exhibited improvements in embryonic myosin heavy chain staining (eMyHC), a protein expressed in fetal and newly regenerating adult muscle fibers (Sartore et al., 1982, Nature, 298: 294) (FIG. 3L). Finally, compared to controls, MuSCs transplanted from NR-treated aged mice into Mdx mice (FIG. 3M), a mouse model of Duchenne muscular dystrophy, more effectively replenished the MuSC compartment and stimulated myogenesis of dystrophin-positive myo fibers, demonstrating an improved engraftment potential for NR-treated MuSCs (FIG. 3N).

This data demonstrate that NR can attenuate the loss of MuSC numbers during aging, enhanced muscle function, improve muscle regeneration after induced muscle damage, improved the stemness of the aged MuSCs and MuSC transplantation efficiency.

Example 3

NR Prevents MuSCs Senescence

The effect of a mitochondrial UPR$^{mt}$ inducing agent of the invention in the prevention of MuSC senescence during aging was studied as follows:

Animals and FACS based muscle stem cell isolation as described in Example 1.

Histology. TA muscles were harvested and the immunestaining was performed as described in Example 2. The following antibodies were used: anti-γH2AX Ser 139 (Millipore), anti-activated-caspase3 (Cell signaling). Secondary antibodies were coupled to Alexa-488 or Alexa-568 fluorochromes (Life technology), and nuclei were stained with DAPI (Invitrogen).

β-galactosidase assay. MuSCs were sorted directly and cultured primary MuSCs were grown on 8 chamber slides (Thermo Scientific). Senescence-associated β-galactosidase activity was detected using the senescence β-galactosidase staining kit (Cell signaling), according to manufacturer's instructions.

Myogenesis assay. Five MuSCs were sorted directly into wells of a Matrigel-coated 96-well cell culture plate, containing MuSC growth medium (F10, 20% FBS, 2.5 ng/ml bFGF, 1×pen/strep), using the automated cell deposition unit (ACDU) of the FACSAria II instrument (BD Biosciences). Cells were cultured at 37° C. for 5 days. Cell colony formations were counted using the DM IL LED Inverted Microscope (Leica) after fixation in freshly made or defrosted 4% paraformaldehyde (PFA) for 10 min.

Cell culture and treatments. FACS sorted MuSCs were grown on a 10% Matrigel (Corning)-coated dish and flasks with Fams F-10 media (Gibco), supplemented with 20% fetal bovine serum (FBS, Gibco), 2.5 ng/ml basic fibroblast growth factor (bFGF, Sigma) and penicillin/streptomycin (1×, Gibco). Dishes were coated with 10% growth factor-free Matrigel solution on ice for 7 min then transferred to a 37° C. cell culture incubator overnight before use. Cells were grown for three generations in vitro before experiments with cells plated and passaged at $10^3$ cells/ml and 50% confluencies, respectively. C2C12 mouse myoblasts were grown in DMEM (4.5 g/l glucose, Gibco) supplemented with 10% FBS and penicillin/streptomycin (1×, Gibco).

Western blotting. C2C12 cells were lysed in a buffer composed of 50 mM Tris, 150 mM KCl, EDTA 1 mM, NP40 1%, nicotinamide 5 mM, sodium butyrate 1 mM and protease inhibitors cocktail (Roche) at pH 7,4. Proteins were separated by SDS-PAGE and transferred onto nitrocellulose membranes. Blocking and antibody incubations were performed in 3% BSA. The following primary antibodies were used: anti-cleavage caspase 3 (Cell Signalling); Anti-γH2AX (Millipore); anti-β-actin (Sigma). All secondary antibodies were from Jackson Immunoresearch. Antibody detection reactions were developed by enhanced chemiluminescence (Advansta, Calif., USA) using x-ray films or imaged using the c300 imaging system (Azure Biosystems).

Figure 4:
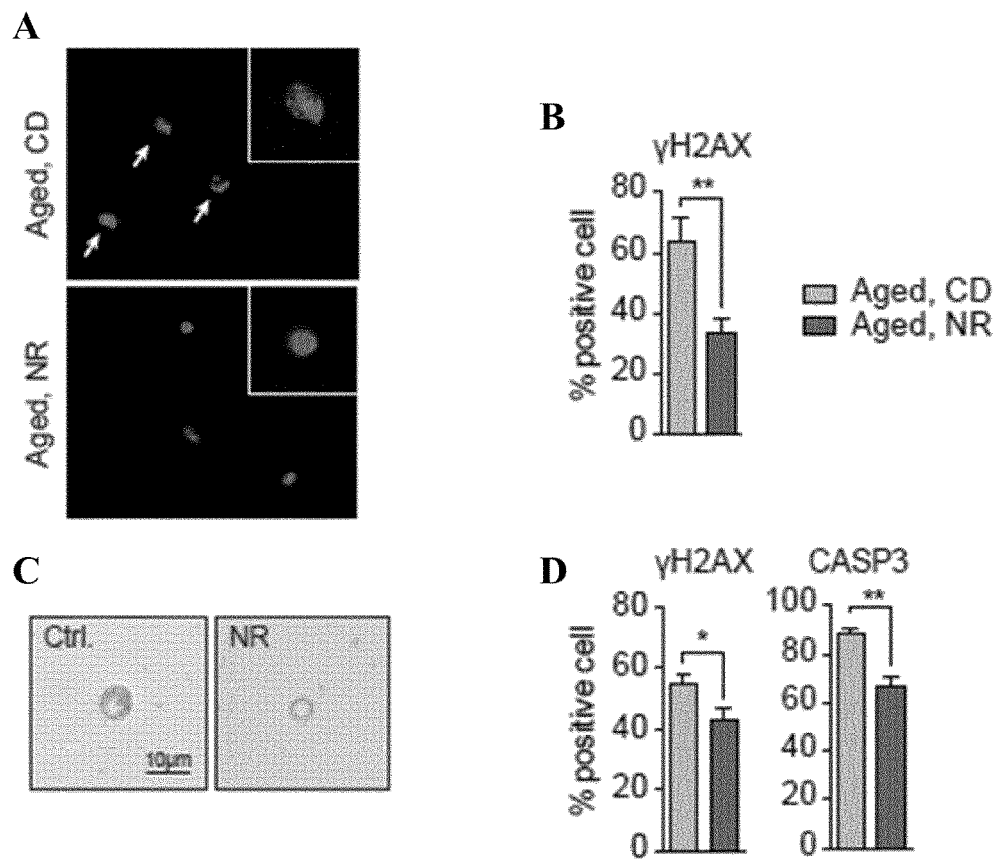
FIG. 4 shows that NR treatment prevents MuSC senescence by increasing mitochondrial respiration. A-B: Immunostaining (A, γH2AX indicated by arrows) and quantification (B) of γH2AX staining in freshly sorted MuSCs from aged mice. 20×20 μm insets show single MuSCs. C: β-galactosidase staining of freshly sorted MuSCs from aged mice. D-E, Quantification (D) of γH2AX and cleaved CASP3 immunostained (E) primary MuSCs, isolated from control or NR-treated aged mice and cultured in vitro for three generations. Scale bar=10 μm. F: Western blots showing the expression of γH2AX, cleaved caspase3, and β-actin in C2C12 myoblasts upon NR treatment at the indicated time points. G: Colony formation ability assay in freshly FACS sorted MuSCs from aged mice control or treated with NR. H-I: Quantification of transcript expression for cell senescence markers (H) or mitochondrial OXPHOS and TCA genes (I) in aged MuSCs isolated from mice treated with NR. J: Basal and uncoupled oxidative respiration and glycolysis, based on OCR and extracellular acidification rate (ECAR), in C2C12 myoblasts that were challenged with PBS or NR for 6 hours (control-white bars; NR-black bars). All data are represented as mean±s.e.m. *p<0.05, **p<0.01. A-E, n=3 mice per group; G, n=24 in each group; H and I, n=6 mice per group.
Figure 4:
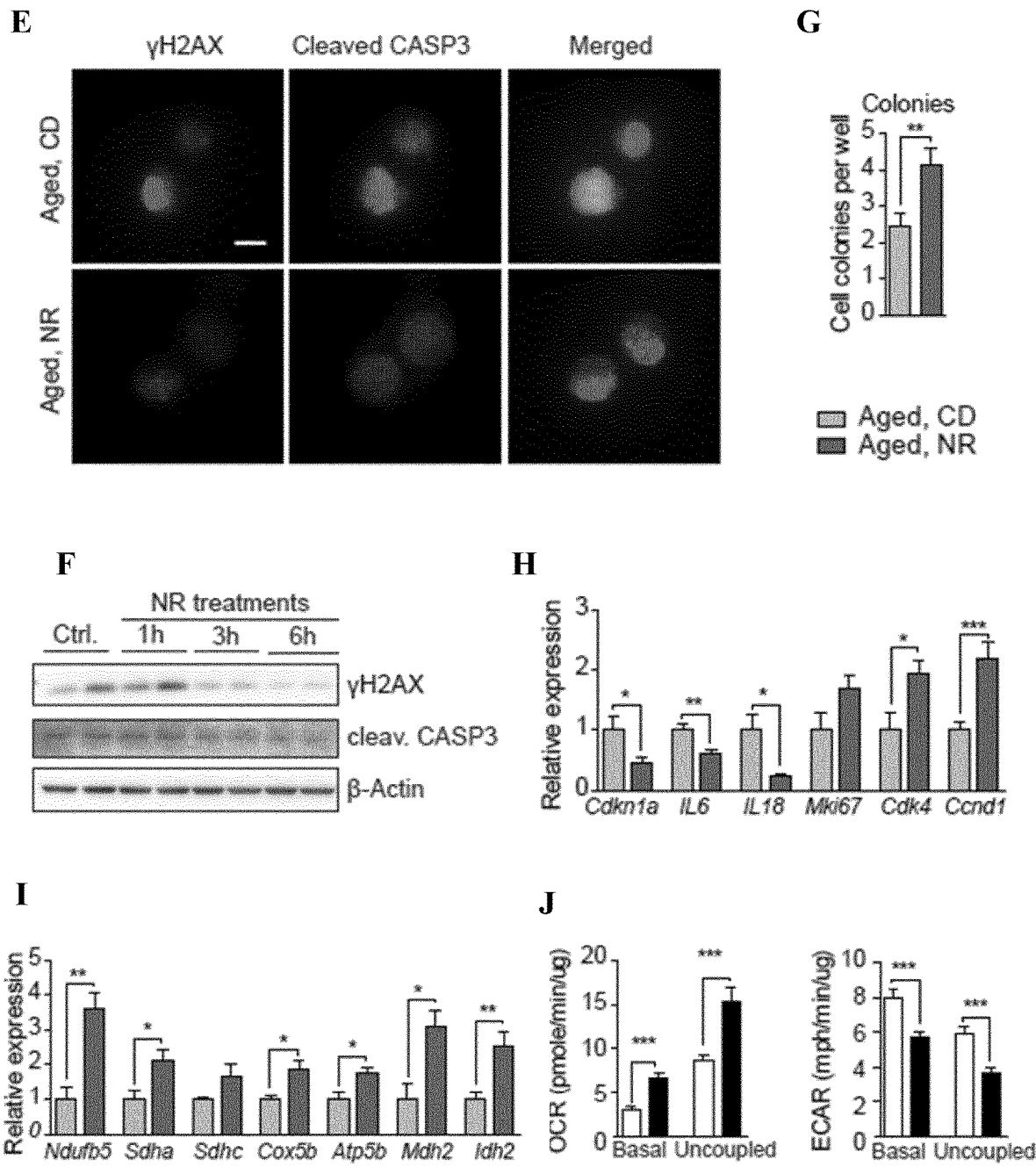

To explain the improvements in aged MuSCs following NR treatment, the ability of NR to prevent MuSC senescence was examined. Freshly isolated MuSCs from NR-treated young and aged mice were immunostained with γH2AX, a marker of DNA damage (Kuilman et al., supra). γH2AX positive nuclei were more abundant in aged MuSCs, yet staining was reduced with NR treatment (FIG. 4A, B). The reduction of the nuclear damage response was confirmed by β-galactosidase staining, a classical senescence marker (Kuilman et al., supra) (FIG. 3C). To evaluate whether the effect of NR on MuSC senescence depends on the in vivo environment (MuSC niche), isolated MuSCs from untreated or NR-treated mice were cultured them ex vivo for three generations. Again, reductions in γH2AX positive nuclei and cleaved caspase-3 (CASP3) (a marker for apoptosis or cell death) immunostaining was found, in MuSCs isolated from NR-treated mice (FIG. 3D, E). Moreover, a 6-hour NR treatment in late passage C2C12 myoblasts reduced the expression of cell senescence and apoptosis markers (Hara et al., 1996, *Molecular and Cellular Biol.*, 16: 859) (FIG. 3F). This is further supported by the enhanced proliferation ability of MuSCs isolated from NR-treated aged mice, as indicated by their enhanced potential to form myogenic colonies (FIG. 3G).

As the in vitro culture conditions do not change the stemness under in vivo treatments, it supports that NR would exert a protective effect against MuSC senescence that is not dependent on extrinsically mediated factors.

Example 4

Rejuvenating MuSCs by Activating the UPR$^{mt}$ and Prohibitin Pathways

The effect of a mitochondrial UPR$^{mt}$ inducing agent of the invention in the rejuvenation of MuSCs was studied as follows:

Animals, FACS based muscle stem cell isolation and gene expression analyses as described in Example 1.

Western blotting performed as described in Example 3. The following primary antibodies were used: anti-HSP60 (Enzo Life Science); anti-β-actin (Sigma); anti-PHB (Biolegend); anti-PHB2 (Santa Cruz); anti-CKD4 (Novus biologicals); anti-CCND1 (Santa Cruz); anti-CCND3 (Santa Cruz); anti-HSP90 (BD Biosciences); HSP70 (Abcam); and anti-CLPP (Sigma).

Cell culture and treatments were prepared according to description of Example 3. C2C12 mouse myoblasts were grown in DMEM (4.5 g/l glucose, Gibco) supplemented with 10% FBS and penicillin/streptomycin (1×, Gibco). Cell transformation with Phb (Santa Cruz) and Phb2 shRNA (Santa Cruz) were performed using jetPEI DNA transfection kit (Polyplus), according to manufacturer's instructions. Cells were treated with 1 mM NR or PBS for 6 hours before cell harvesting or fixation. Respirometry on C2C12 myoblasts. Basal and uncoupled oxygen consumption rates (OCRs) and the extracellular acidification rate (ECAR) was measured using the Seahorse extracellular flux bioanalyzer (XF96, Seahorse Bioscience Inc.). To uncouple mitochondria, 5 uM of FCCP was injected after a basal respiration measurement. All measurements were performed in triplicates and results were normalized to total protein amount (C2C12 cells), assessed using a Bradford kit (Bio-Rad).

Figure 5:
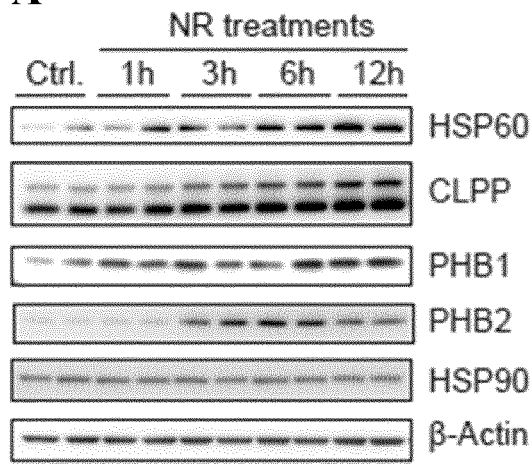
FIG. 5 shows that effects of NR on MuSC senescence are mediated by prohibitin activation of UPR$^{mt}$. A: Expression of HSP60, CLPP and prohibitins in C2C12 myoblasts upon NR treatment at the indicated time points. B: Quantification of transcript expression for UPR$^{mt}$ and prohibitin genes in MuSCs from aged (22-24 months old) C57BL/6J mice following 6 weeks of chow or NR supplemented (400 mg/kg/day) diets. C: Expression of prohibitins and cell cycle related genes in C2C12 myoblasts after a combined Phb1 and Phb2 shRNA knockdown in combination with a 6-hour NR treatment. D: Expression of prohibitins and cell cycle related genes in C2C12 myoblasts with the combined overexpression of Phb1 and Phb2. All data are represented as mean±s.e.m. *p<0.05, **p<0.01. B, n=6 mice per group.
Figure 5:
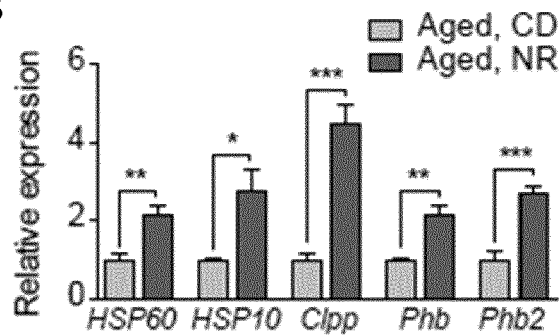
Figure 5:
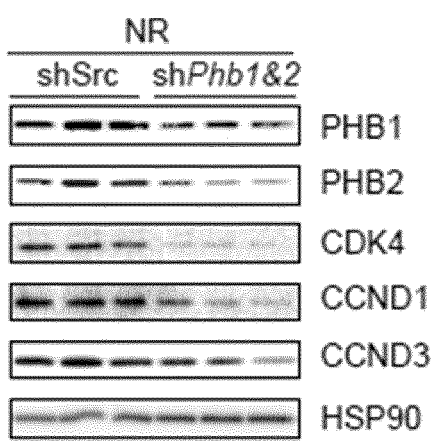
Figure 5:
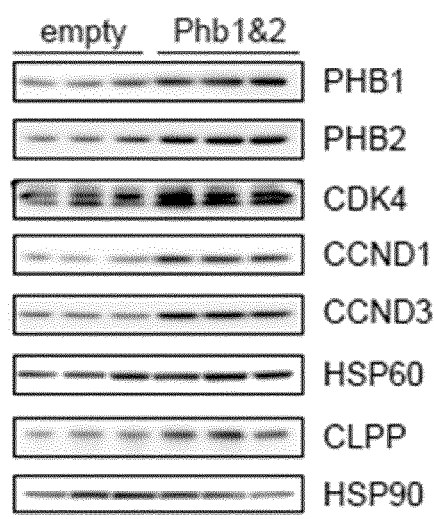

In contrast to the up-regulated CDKN1A senescence pathway seen in aged MuSCs (FIG. 2D), NR significantly reduced mRNA levels of CDKN1A, and related senescence indicators, while increasing the expression of cell cycle related genes, in freshly isolated MuSCs (FIG. 4H). This protective effect of NR on MuSC senescence relies on changes in mitochondrial function as NR largely rescued mitochondrial TCA and OXPHOS gene expression in aged MuSCs (FIG. 4I). This is consistent with increases in oxidative respiration and reductions in glycolysis in NR-treated C2C12 cells (FIG. 4J). The trend in oxidative respiration was replicated in primary MuSCs isolated from NR-treated aged mice. As the mitochondrial unfolded protein response (UPR$^{mt}$) is known to be induced by NR (Mouchiroud et al., supra), several UPR$^{mt}$ markers were similarly induced in NR-treated C2C12 mouse myoblasts (FIG. 5A). The mechanism of how UPR$^{mt}$ regulates senescence was tested examining its effect on prohibitins, a family of stress response proteins. Prohibitins are known to sense mitochondria stress and modulate senescence in fibroblasts in mammals (Coates et al., 2001, *Exp. Cell Res.*, 265: 268). Intriguingly, the expression of prohibitins, Phb1 and Phb2, is significantly reduced in the bioinformatics analysis (FIG. 1E), and in freshly isolated aged MuSCs. However, NR treatment induced Phb1 and Phb2 expression in both young and aged MuSCs (FIG. 5B) and in C2C12 myoblasts (FIG. 5A), consistent with the upregulation of UPR$^{mt}$ markers and cell cycle genes. The effects of NR on cell senescence were furthermore PHB-dependent, as knockdown and overexpression of prohibitins inhibits and stimulates cell cycle gene expression, respectively (FIG. 5C, D).

These results indicate that NR activates UPR$^{mt}$ and the prohibitin signaling pathway, thereby reversing MuSC senescence.

Example 5

NR Reprograms Senescence Prone MuSCs in Mdx Mice

The effect of a mitochondrial UPR$^{mt}$ inducing agent of the invention in reprogramming of senescence of MuSCs was studied as follows:

Animals, FACS based muscle stem cell isolation as described in Example 1.

β-galactosidase assay as described in Example 3.

Cardiotoxin-induced muscle damage and Histology as described in Example 2. The following antibodies were used: anti-eMHC (Developmental Studies Hybridoma Bank, DSHB, University of Iowa), anti-Pax7 (DSHB, University of Iowa), anti-γH2AX Ser 139 (Millipore) and anti-activated-caspase3 (Cell signaling).

Figure 6:
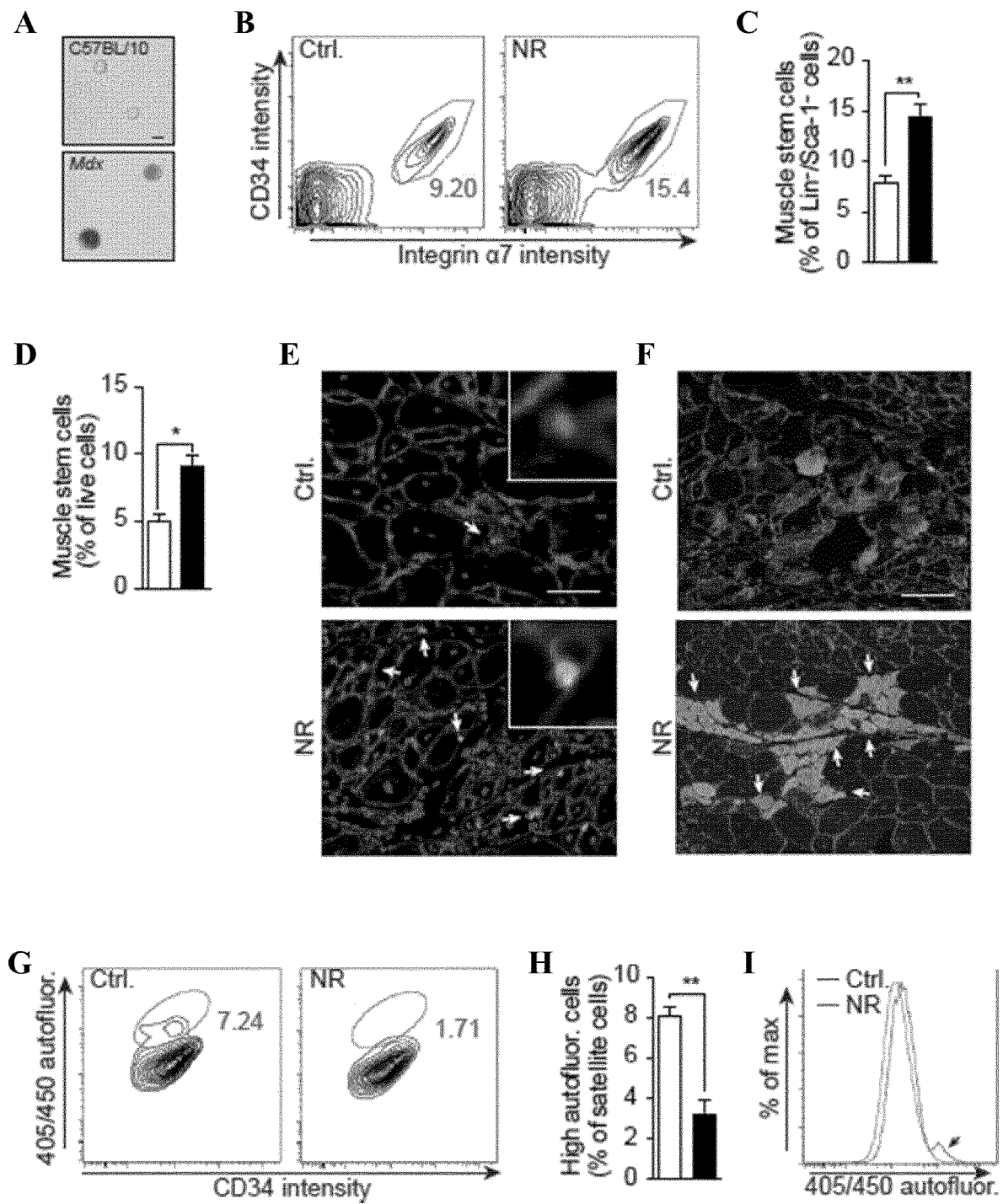
FIG. 6 shows increased stem cell number and stemness in NR-treated Mdx mice. Mdx mice (one-months-old) received a dietary supplement with NR (400 mg/kg/day) for 10 weeks. All results are compared to Mdx mice given a control diet. A: β-galactosidase staining of MuSCs isolated from C57BL/10SnJ or Mdx mice and cultured in vitro for three generations. Scale bar=10 μm. B-D: FACS contour plots of Sca-1$^-$, Lin$^-$(CD11b$^-$ CD23$^-$, CD45$^-$) cells isolated from muscle tissue. Percentage of the CD34$^+$/integrin α7$^+$/Lin$^-$/Sca-1$^-$ MuSC populations are noted in in contour plots (B), and quantified relative to the total Lin$^-$/Sca-1$^-$ cell population (C) or to the entire live cell population (D), control-white bars, NR-black bars. E-F: Immunostaining of muscle stem cells (PAX7) (E) and newly regenerated muscle fibers (eMyHC) (F) in tissue-sections of NR-treated Mdx mice 7 days after CTX-induced muscle damage. Arrows point to PAX7$^+$ MuSCs (E) and eMyHC (F). 20×20 μm insets show single MuSCs. Scale bar=50 μm. G-I: FACS contour plots (G), quantification (H) and distribution (I) of MuSC autofluorescence as a measure of the relative NAD(P)H concentration upon UV light excitation. Autofluorescence emission was detected using 405/450 nm. Arrow in (I) points to the highly autofluorescent stem cell population. J: β-galactosidase staining of FACS-sorted MuSCs from C57BL/6 (B6), untreated (Mdx) or NR-treated Mdx (Mdx with NR) mice challenged with PBS or NR for 6 hours. K: Immunostaining showing γH2AX and cleaved caspase-3 in MuSCs cultured in vitro for three generations. Arrow points to a γH2AX-positive nucleus. Scale bar=10 μm. L: Muscle structure in tissue-sections from NR-treated Mdx mice with 7 days of recovery following CTX induced muscle damage. Images show representative H/E staining of muscle cross sections. Scale bar=100 μm. All data are represented as mean±s.e.m. *p<0.05, **p<0.01. A-I and K-L, n=3-5 per treatment group; J, n=3 mice and n=6 in vitro treatments.
Figure 6:
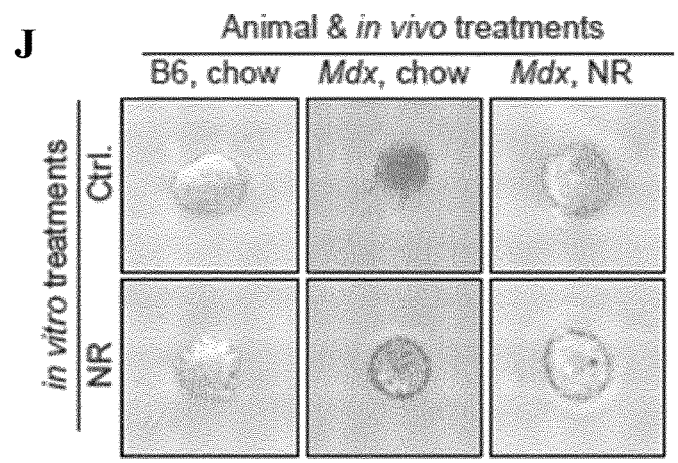
Figure 6:
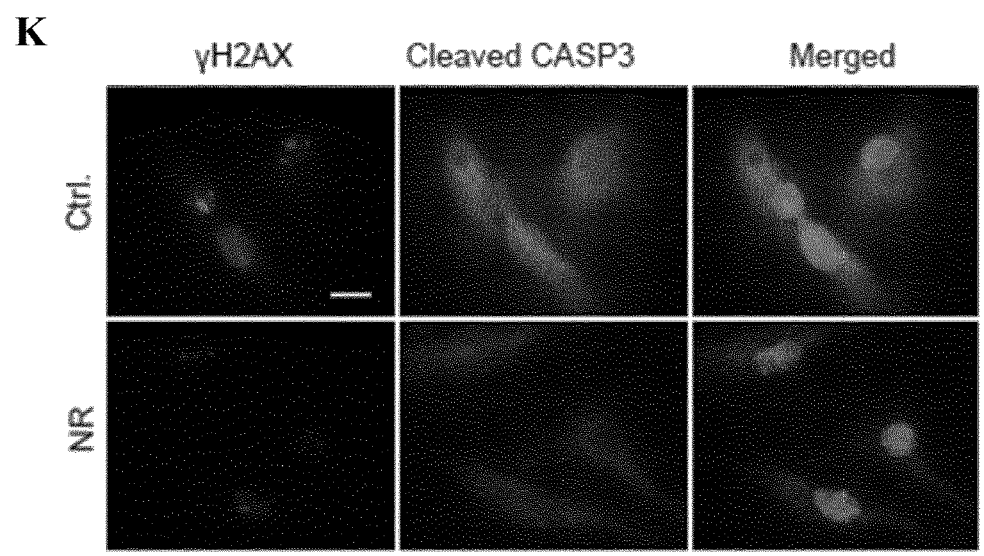
Figure 6:
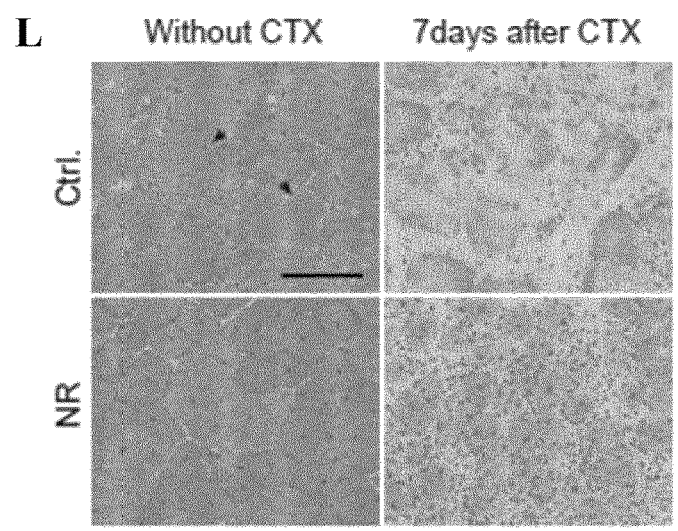

Determining cellular redox ratio. NAD+ and NADH quantification and ratio were measured using a kit from Biovision (Milpitas, Calif.), following providers' instructions. With continuous muscle regeneration, MuSCs in Mdx mice are abnormally active at a young age, leading to MuSC depletion and dysfunction later in life. As a result, primary MuSCs isolated from 14-week-old Mdx mice were significantly more senescent compared to control mice (FIG. 6A). Similar to the effect in aged animals, NR treatment of Mdx mice increased MuSC numbers by ~1.8 fold in vivo (FIG. 6B-D), as also confirmed by PAX7 immunostaining (FIG. 6E). Along with the increase in MuSCs, there was an increase in regenerated muscle fibers following NR treatment (FIG. 6F). Thus the self-renewal capacity of Mdx mouse MuSCs was tested. The cellular redox ratio decreases as MuSCs differentiate (Fulco et al., 2003, *Molecular Cell*, 12: 51), which can be detected by the increase in 405/450 autofluorescence (Quinn et al., 2013, *Scientific Reports*, 3: 3432). In line with NR increasing Mdx mouse MuSC numbers, we found a significant reduction in autofluorescence from MuSCs isolated from these animals (FIG. 6G-I).

We then performed β-galactosidase staining on primary MuSCs isolated from Mdx mice, with or without NR treatment, and cultured these cells with NR or vehicle in vitro. This demonstrated that MuSCs isolated from NR-treated mice were less prone to senescence (FIG. 6J). In addition, when these MuSCs were treated with NR in vitro there was a further reduction in senescence (FIG. 6J). The prevention of MuSCs senescence in NR-treated Mdx mice was confirmed by the attenuation of γH2AX and cleaved caspase-3 immunostaining (FIG. 6K). To evaluate MuSC function, CTX-induced muscle regeneration was examined in NR-treated mice. Consistent with the prevention of MuSC senescence, muscle regeneration was improved with NR (FIG. 6L).

These results show that NR treatment can increase MuSCs numbers in mouse model of Duchenne muscular dystrophy and further prevent MuSCs senescence.

Example 6

Thiamphenicol Induces UPR$^{mt}$ in Myoblasts

The activity of TAP as another a mitochondrial UPR$^{mt}$ inducing agent of the invention in was assayed in myoblast as follows:

Western blotting. C2C12 cells were lysed in a buffer composed of 50 mM Tris, 150 mM KCl, EDTA 1 mM, NP40 1%, nicotinamide 5 mM, sodium butyrate 1 mM and protease inhibitors cocktail (Roche) at pH 7,4. Proteins were separated by SDS-PAGE and transferred onto nitrocellulose membranes. Blocking and antibody incubations were performed in 3% BSA. The following primary antibodies were used: anti-cleavage caspase 3 (Cell Signalling); Anti-γH2AX (Millipore); anti-β-actin (Sigma). All secondary antibodies were from Jackson Immunoresearch. Antibody detection reactions were developed by enhanced chemiluminescence (Advansta, Calif., USA) using x-ray films or imaged using the c300 imaging system (Azure Biosystems).

The following primary antibodies were used: anti-HSP60 (Enzo Life Science); anti-PHB (Biolegend); anti-PHB2 (Santa Cruz); anti-CKD4 (Novus biologicals); anti-CCND1 (Santa Cruz); anti-CCND3 (Santa Cruz); anti-HSP90 (BD Biosciences); HSP70 (Abcam); anti-MT-CO1 (Bio legend); anti-ATP5A (Bio legend); anti-Grp78 (Abcam); and anti-CLPP (Sigma).

Figure 7:
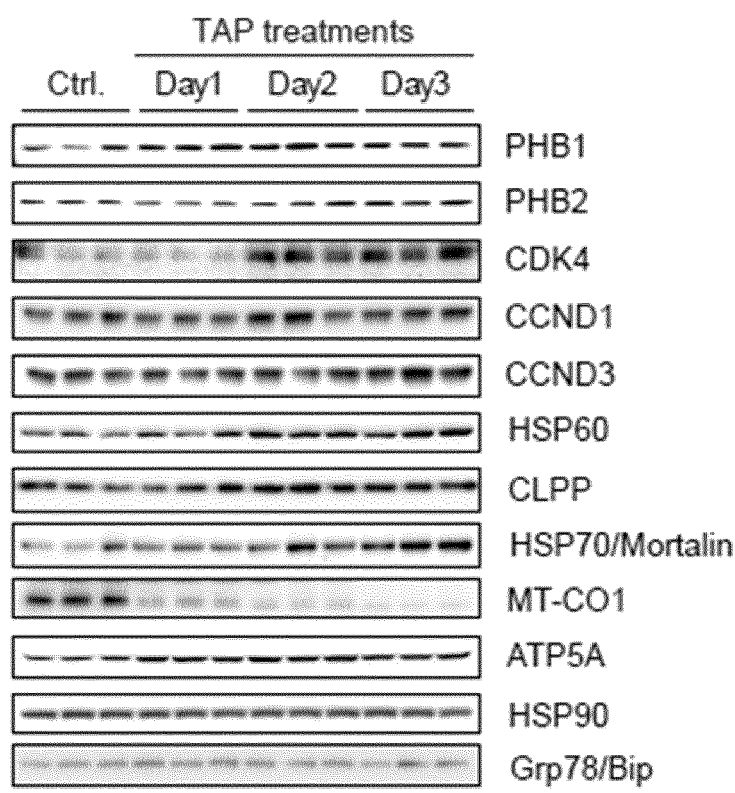
FIG. 7 shows expression of prohibitins and cell cycle related genes in C2C12 myoblasts following different treatment periods with 50 μg/ml TAP, which induces a mitonuclear imbalance and UPR$^{mt}$.

UPR$^{mt}$ induction by thiamphenicol (TAP) which also induced prohibitins and cell cycle gene expression in C2C12 cells (FIG. 7) is supporting the ability of this agent in attenuating the senescence-signaling cascade in those cells.

These results support that TAP can be used as another mitochondrial UPR$^{mt}$ inducing agent and would be able to MuSC senescence.

---

Sequence listing

Nucleic acid sequence of 36b4 forward primer
SEQ ID NO: 1: AGATTCGGGATATGCTGTTGG Nucleic acid sequence of 36b4 reverse primer
SEQ ID NO: 2: AAAGCCTGGAAGAAGGAGGTC Nucleic acid sequence of Ndufb5 forward primer
SEQ ID NO: 3: CTTCGAACTTCCTGCTCCTT Nucleic acid sequence of Ndufb5 reverse primer
SEQ ID NO: 4: GGCCCTGAAAAGAACTACG -continued

Sequence listing

Nucleic acid sequence of Sdha forward primer
SEQ ID NO: 5: GGAACACTCCAAAAACAGACCT Nucleic acid sequence of Sdha reverse primer
SEQ ID NO: 6: CCACCACTGGGTATTGAGTAGAA Nucleic acid sequence of Sdhc forward primer
SEQ ID NO: 7: GCTGCGTTCTTGCTGAGACA Nucleic acid sequence of Sdhc reverse primer
SEQ ID NO: 8: ATCTCCTCCTTAGCTGTGGTT Nucleic acid sequence of Cox5b forward primer
SEQ ID NO: 9: AAGTGCATCTGCTTGTCTCG Nucleic acid sequence of Cox5b reverse primer
SEQ ID NO: 10: GTCTTCCTTGGTGCCTGAAG Nucleic acid sequence of Atp5b forward primer
SEQ ID NO: 11: GGTTCATCCTGCCAGAGACTA Nucleic acid sequence of Atp5b reverse primer
SEQ ID NO: 12: AATCCCTCATCGAACTGGACG Nucleic acid sequence of Mdh2 forward primer
SEQ ID NO: 13: TTGGGCAACCCCTTTCACTC Nucleic acid sequence of Mdh2 reverse primer
SEQ ID NO: 14: GCCTTTCACATTTGCTCTGGTC Nucleic acid sequence of Idh2 forward primer
SEQ ID NO: 15: GGAGAAGCCGGTAGTGGAGAT Nucleic acid sequence of Idh2 reverse primer
SEQ ID NO: 16: GGTCTGGTCACGGTTTGGAA Nucleic acid sequence of Idh3a forward primer
SEQ ID NO: 17: CCCATCCCAGTTTGATGTTC Nucleic acid sequence of Idh3a reverse primer
SEQ ID NO: 18: ACCGATTCAAAGATGGCAAC Nucleic acid sequence of Cdkn1a forward primer
SEQ ID NO: 19: GTGGGTCTGACTCCAGCCC Nucleic acid sequence of Cdkn1a reverse primer
SEQ ID NO: 20: CCTTCTCGTGAGACGCTTAC Nucleic acid sequence of Mki67 forward primer
SEQ ID NO: 21: TTGGAAAGGAACCATCAAGG Nucleic acid sequence of Mki67 reverse primer
SEQ ID NO: 22: TTTCTGCCAGTGTGCTGTTC Nucleic acid sequence of Cdk4 forward primer
SEQ ID NO: 23: CCGGTTGAGACCATTAAGGA Nucleic acid sequence of Cdk4 reverse primer
SEQ ID NO: 24: CACGGGTGTTGCGTATGTAG Nucleic acid sequence of Ccna2 forward primer
SEQ ID NO: 25: AAGAGAATGTCAACCCCGAAA Nucleic acid sequence of Ccna2 reverse primer
SEQ ID NO: 26: ACCCGTCGAGTCTTGAGCTT Nucleic acid sequence of Ccnd1 forward primer
SEQ ID NO: 27: GAGCGTGGTGGCTGCGATGCAA Nucleic acid sequence of Ccnd1 reverse primer
SEQ ID NO: 28: GGCTTGACTCCAGAAGGGCTTCAAT Nucleic acid sequence of Ccne1 forward primer
SEQ ID NO: 29: CAAAGCCCAAGCAAAGAAAG Sequence listing Nucleic acid sequence of Ccne1 reverse primer
SEQ ID NO: 30: CCACTGTCTTTGGAGGCAAT Nucleic acid sequence of Cdc6 forward primer
SEQ ID NO: 31: GACACAAGCTACCATGGTTT Nucleic acid sequence of Cdc6 reverse primer
SEQ ID NO: 32: CAGGCTGGACGTTTCTAAGTT Nucleic acid sequence of IL6 forward primer
SEQ ID NO: 33: GGTGACAACCACGGCCTTCCC Nucleic acid sequence of IL6 reverse primer
SEQ ID NO: 34: AAGCCTCCGACTTGTGAAGTGGT Nucleic acid sequence of IL18 forward primer
SEQ ID NO: 35: GTGAACCCCAGACCAGACTG Nucleic acid sequence of IL18 reverse primer
SEQ ID NO: 36: CCTGGAACACGTTTCTGAAAGA Nucleic acid sequence of Hsp60 forward primer
SEQ ID NO: 37: ACAGTCCTTCGCCAGATGAGAC Nucleic acid sequence of Hsp60 reverse primer
SEQ ID NO: 38: TGGATTAGCCCCTTTGCTGA Nucleic acid sequence of Hsp10 forward primer
SEQ ID NO: 39: CTGACAGGTTCAATCTCTCCAC Nucleic acid sequence of Hsp10 reverse primer
SEQ ID NO: 40: AGGTGGCATTATGCTTCCAG Nucleic acid sequence of Clpp forward primer
SEQ ID NO: 41: CACACCAAGCAGAGCCTACA Nucleic acid sequence of Clpp reverse primer
SEQ ID NO: 42: TCCAAGATGCCAAACTCTTG Nucleic acid sequence of Phb forward primer
SEQ ID NO: 43: TCGGGAAGGAGTTCACAGAG Nucleic acid sequence of Phb reverse primer
SEQ ID NO: 44: CAGCCTTTTCCACCACAAAT Nucleic acid sequence of Phb2 forward primer
SEQ ID NO: 45: CAAGGACTTCAGCCTCATCC Nucleic acid sequence of Phb2 reverse primer
SEQ ID NO: 46: GCCACTTGCTTGGCTTCTAC

The invention claimed is:

1. A method of cell-based therapy, said method comprising administering or grafting a skeletal muscle stem cell composition comprising skeletal muscle stem cells and at least one $UPR^{mt}$ inducing agent selected from nicotinamide riboside (NR), thiamphenicol (TAP) and analogues thereof to a subject.

2. A method of cell-based therapy in a subject, said method comprising administering a composition comprising at least one $UPR^{mt}$ inducing agent selected from nicotinamide riboside (NR), thiamphenicol (TAP) and analogues thereof and wherein said at least one $UPR^{mt}$ inducing agent is administered in combination with one or more replacement therapies using allogenic or autologous muscle stem cells.

3. The method according to claim 1, wherein said at least one UPRmt inducing agent is nicotinamide riboside (NR).

4. The method according to claim 1, wherein said at least one UPRmt inducing agent is thiamphenicol (TAP).

5. The method according to claim 2, wherein said at least one UPRmt inducing agent is nicotinamide riboside (NR).

6. The method according to claim 2, wherein said at least one UPRmt inducing agent is thiamphenicol (TAP).

* * * * *